United States Patent
Michelson

(12) 
(10) Patent No.: US 6,716,247 B2
(45) Date of Patent: Apr. 6, 2004

(54) EXPANDABLE PUSH-IN INTERBODY SPINAL FUSION IMPLANT

(76) Inventor: Gary K. Michelson, 438 Sherman Canal, Venice, CA (US) 90291

(*) Notice: Subject to any disclaimer, the term of this patent is extended or adjusted under 35 U.S.C. 154(b) by 23 days.

(21) Appl. No.: 10/258,198

(22) PCT Filed: Feb. 5, 2001

(86) PCT No.: PCT/US01/03657
§ 371 (c)(1),
(2), (4) Date: Apr. 23, 2002

(87) PCT Pub. No.: WO01/56513
PCT Pub. Date: Aug. 9, 2001

(65) Prior Publication Data
US 2003/0208275 A1 Nov. 6, 2003

Related U.S. Application Data

(60) Provisional application No. 60/180,404, filed on Feb. 4, 2000.

(51) Int. Cl.[7] .................................................. A61F 2/28
(52) U.S. Cl. ................... 623/17.16; 623/17.11
(58) Field of Search ........................... 623/17.11–17.16

(56) References Cited

U.S. PATENT DOCUMENTS

| | | |
|---|---|---|
| 3,875,595 A | 4/1975 | Froning |
| 4,309,777 A | 1/1982 | Patil |
| 4,349,921 A | 9/1982 | Kuntz |
| 4,401,112 A | 8/1983 | Rezaian |
| 4,501,269 A | 2/1985 | Bagby |
| 4,553,273 A | 11/1985 | Wu |

(List continued on next page.)

FOREIGN PATENT DOCUMENTS

| | | |
|---|---|---|
| CA | 2151481 | 3/1995 |
| DE | 44 16 605 C1 | 6/1995 |
| FR | 2 717 068 | 9/1995 |
| FR | 2 771 282 | 5/1999 |
| SU | 1424826 A1 | 9/1988 |
| WO | WO 96/27348 | 9/1996 |
| WO | WO 97/00054 | 12/1997 |
| WO | WO 98/34552 | 8/1998 |
| WO | WO 98/48739 | 11/1998 |
| WO | WO 99/42062 | 8/1999 |
| WO | WO 00/12033 | 3/2000 |
| WO | WO 00/35388 | 6/2000 |
| WO | WO 00/35389 | 6/2000 |
| WO | WO 00/66045 | 11/2000 |
| WO | WO 00/74605 | 12/2000 |

OTHER PUBLICATIONS

PCT Search Report dated May 2, 2001 for International Application No. PCT/US01/03657 filed Feb. 5, 2001.
European Search Report for Application EP 01 91 0418, dated Apr. 17, 2003.
U.S. patent application Ser. No. 09/612,188, Filed Jul. 7, 2000.
U.S. patent application Ser. No. 10/011,652, Filed Nov. 6, 2001, WO01/56513.
U.S. patent application Ser. No. 09/551,964, Filed Dec. 31, 2002, 6,500,205.
U.S. patent application Ser. No. 09/574,858, May 19, 2000.
U.S. patetn application Ser. No. 09/772,309, filed Jan. 29, 2001, 2001/0034553.

*Primary Examiner*—Corrine McDermott
*Assistant Examiner*—Thomas Barrett
(74) *Attorney, Agent, or Firm*—Martin & Ferraro, LLP

(57) ABSTRACT

A push-in interbody spinal fusion (100) implant having an expandable height. The implant (100) comprises upper and lower members (102 and 106) with an expander in between (122). When the expander (122) is changed from one position to another, for example as in the first embodiment where it is rotated in a plane perpendicular to the axis of the upper and lower members (102 and 106), the height of the implant (100) is increased.

64 Claims, 24 Drawing Sheets

U.S. PATENT DOCUMENTS

| | | | |
|---|---|---|---|
| 4,554,914 A | 11/1985 | Kapp et al. | |
| 4,636,217 A | 1/1987 | Ogilvie et al. | |
| 4,657,550 A | 4/1987 | Daher | |
| 4,714,469 A | 12/1987 | Kenna | |
| 4,759,769 A | 7/1988 | Hedman et al. | |
| 4,863,476 A | 9/1989 | Shepperd | |
| 4,932,975 A | 6/1990 | Main et al. | |
| 4,961,740 A | 10/1990 | Ray et al. | |
| 5,015,247 A | 5/1991 | Michelson | |
| 5,026,373 A | 6/1991 | Ray et al. | |
| 5,055,104 A | 10/1991 | Ray | |
| 5,059,193 A | 10/1991 | Kuslich | |
| 5,062,850 A | 11/1991 | MacMillan et al. | |
| 5,123,926 A | 6/1992 | Pisharodi | |
| 5,147,402 A | 9/1992 | Bohler et al. | |
| 5,171,278 A | 12/1992 | Pisharodi | |
| 5,192,327 A | 3/1993 | Brantigan | |
| 5,236,460 A | 8/1993 | Barber | |
| 5,258,031 A | 11/1993 | Salib et al. | |
| 5,263,953 A | 11/1993 | Bagby | |
| 5,290,312 A | 3/1994 | Kojimoto et al. | |
| 5,306,310 A | 4/1994 | Siebels | |
| 5,314,477 A | 5/1994 | Marnay | |
| 5,336,223 A | 8/1994 | Rogers | |
| 5,397,364 A | 3/1995 | Kozak et al. | |
| 5,439,684 A | 8/1995 | Prewett et al. | |
| 5,455,231 A | 10/1995 | Constantz et al. | |
| 5,464,439 A | 11/1995 | Gendler | |
| 5,507,813 A | 4/1996 | Dowd et al. | |
| 5,507,816 A | 4/1996 | Bullivant | |
| 5,522,899 A | 6/1996 | Michelson | |
| 5,549,679 A | 8/1996 | Kuslich | |
| 5,554,191 A | 9/1996 | Lahille et al. | |
| 5,593,409 A | 1/1997 | Michelson | |
| 5,609,635 A | 3/1997 | Michelson | |
| 5,653,763 A | 8/1997 | Errico et al. | |
| 5,665,122 A | 9/1997 | Kambin | |
| 5,693,100 A | 12/1997 | Pisharodi | |
| 5,702,391 A | 12/1997 | Lin | |
| 5,702,455 A | 12/1997 | Saggar | |
| 5,713,904 A | 2/1998 | Errico et al. | |
| 5,749,916 A | 5/1998 | Richelsoph | |
| 5,776,199 A | 7/1998 | Michelson | |
| 5,782,832 A | 7/1998 | Larsen et al. | |
| 5,785,710 A | 7/1998 | Michelson | |
| 5,800,550 A | 9/1998 | Sertich | |
| 5,865,848 A | 2/1999 | Baker | |
| 5,885,982 A | 3/1999 | Dolynchuk et al. | |
| 5,928,284 A | 7/1999 | Mehdizadeh | |
| 5,976,187 A | 11/1999 | Richelsoph | |
| 5,980,522 A | 11/1999 | Koros et al. | |
| 5,989,290 A | 11/1999 | Biedermann et al. | |
| 6,015,436 A | 1/2000 | Schonhoffer | |
| 6,019,792 A | 2/2000 | Cauthen | |
| 6,039,761 A * | 3/2000 | Li et al. | 623/17.16 |
| 6,045,579 A | 4/2000 | Hochshuler et al. | |
| 6,080,193 A | 6/2000 | Hochshuler et al. | |
| 6,087,555 A | 7/2000 | Dunstan et al. | |
| 6,093,207 A | 7/2000 | Pisharodi | |
| 6,102,950 A | 8/2000 | Vaccaro | |
| 6,117,174 A | 9/2000 | Nolan | |
| 6,126,689 A * | 10/2000 | Brett | 623/17.16 |
| 6,129,763 A | 10/2000 | Chauvin et al. | |
| 6,176,882 B1 | 1/2001 | Biedermann et al. | |
| 6,183,517 B1 | 2/2001 | Suddaby | |
| 6,190,414 B1 | 2/2001 | Young et al. | |
| 6,190,880 B1 | 2/2001 | Israel et al. | |
| 6,193,757 B1 | 2/2001 | Foley et al. | |
| 6,201,039 B1 | 3/2001 | Brown et al. | |
| 6,375,683 B1 * | 4/2002 | Crozet et al. | 623/17.15 |
| 6,419,705 B1 | 7/2002 | Erickson | |
| 6,436,140 B1 | 8/2002 | Liu et al. | |
| 6,491,724 B1 * | 12/2002 | Ferree | 623/17.11 |

* cited by examiner

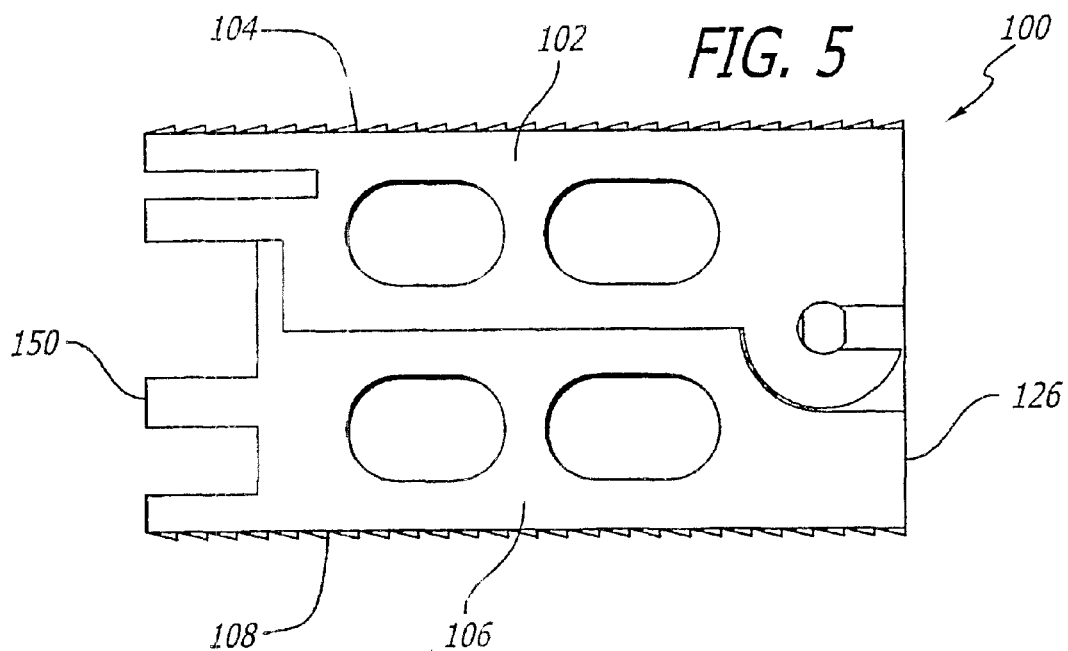
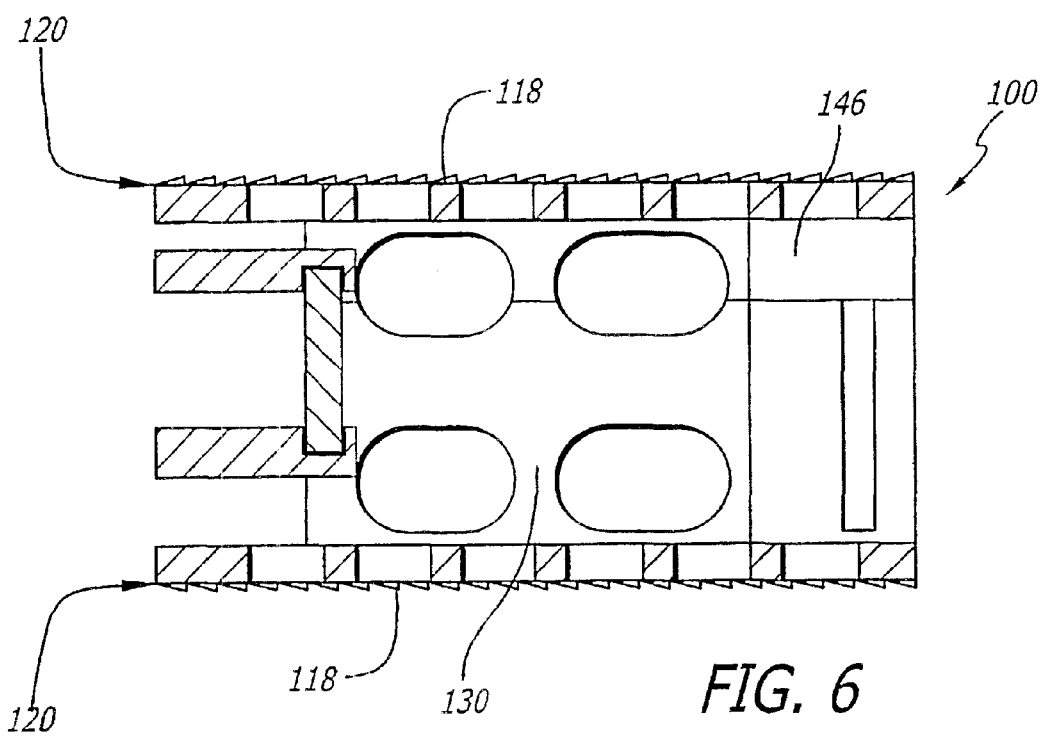

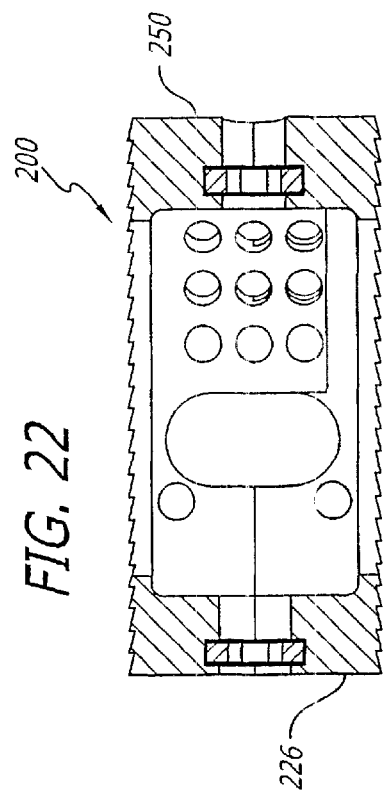
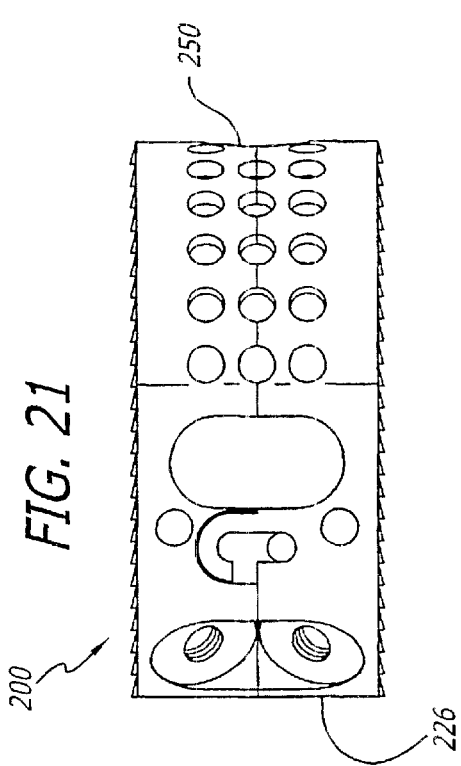
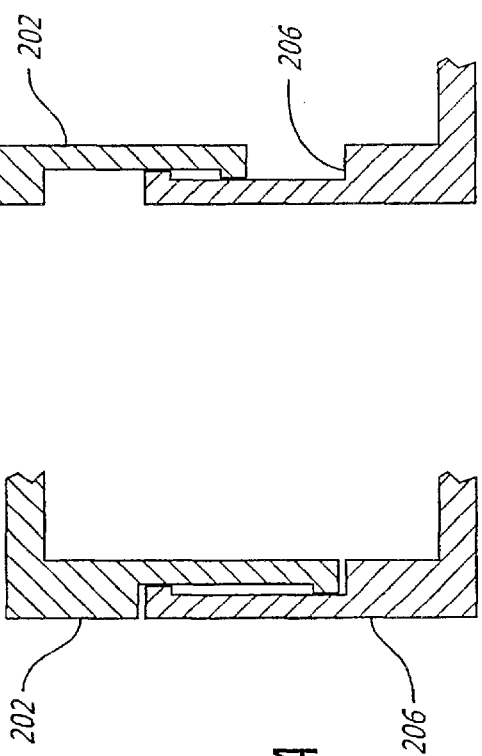

FIG. 24
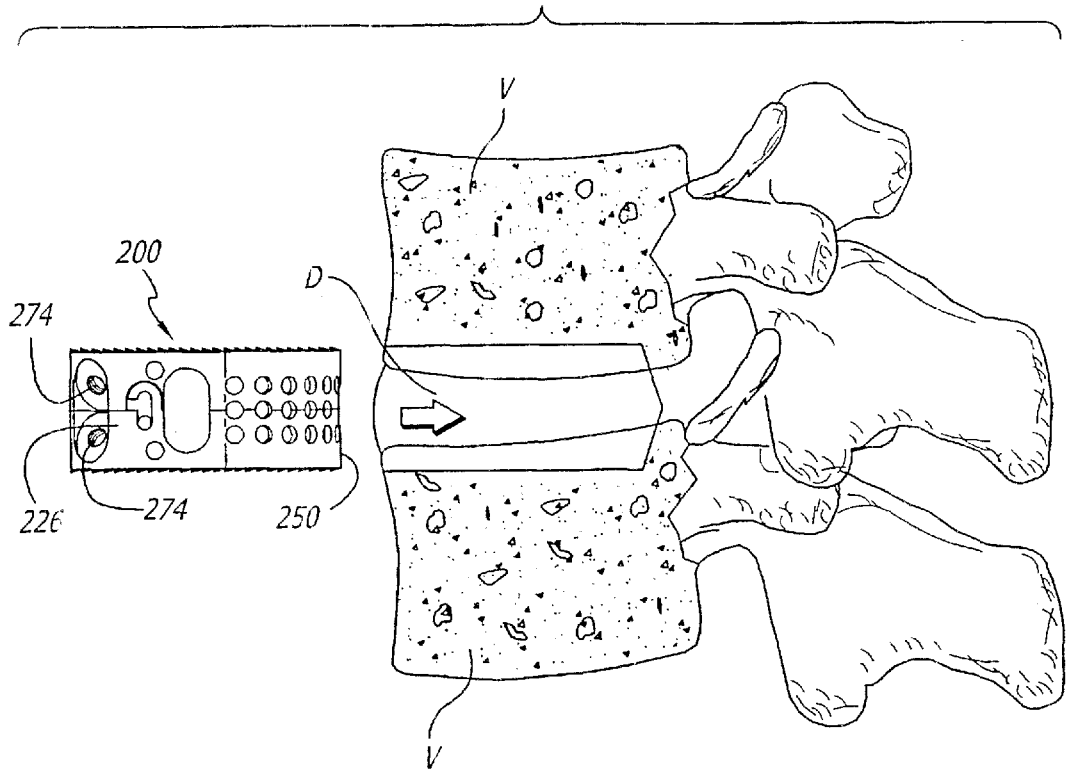
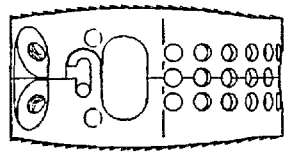
FIG. 24A
FIG. 25
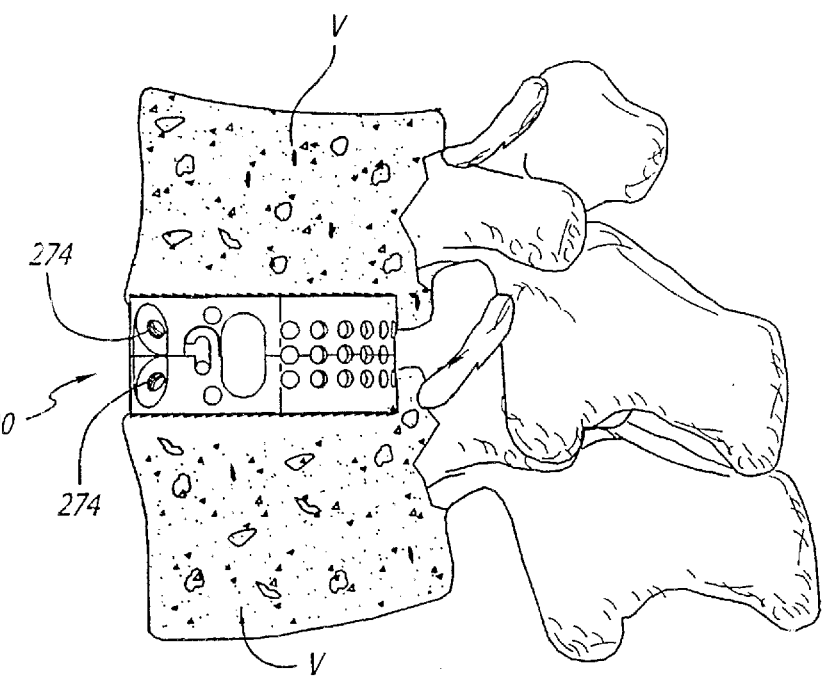

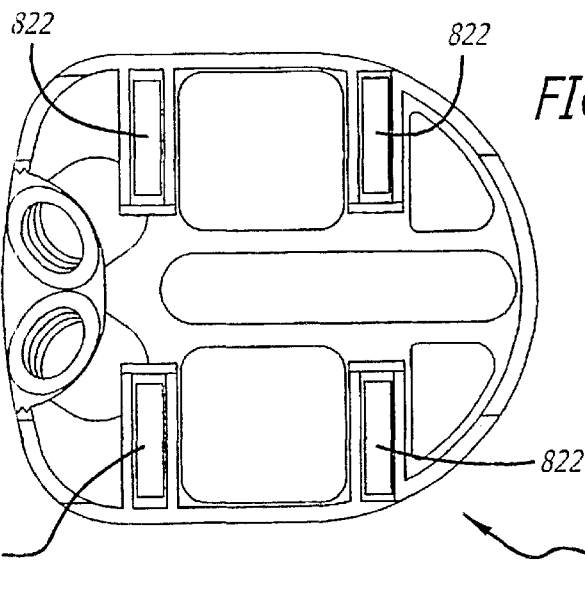
FIG. 46
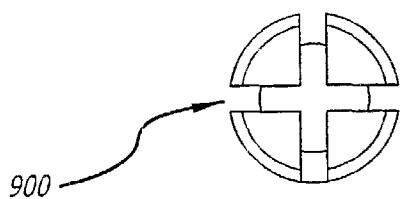
FIG. 47
FIG. 48
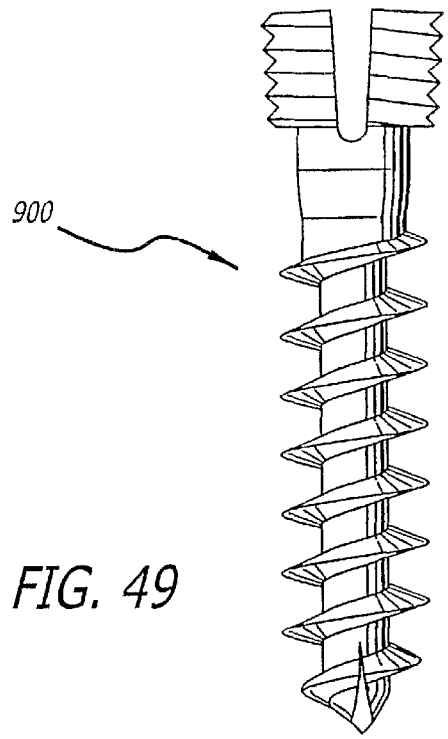
FIG. 49

EXPANDABLE PUSH-IN INTERBODY SPINAL FUSION IMPLANT

This application claims the benefit of U.S. Provisional Application No. 60/180,404, filed Feb. 4, 2000, incorporated herein by reference.

BACKGROUND OF THE INVENTION

1. Field of the Invention

The present invention relates generally to an improved push-in interbody (for placement at least in part between adjacent vertebral bodies in the space previously occupied by disc material) spinal fusion implant for the immobilization of vertebrae. The present invention is directed to expandable push-in implants only not including push-in implants having substantially arcuate upper and lower members oriented toward the adjacent vertebral bodies and designed to engage the vertebral bodies along arcuate cuts therein typically formed by a drill. Further, the present invention is not directed to threaded implants requiring rotation for insertion into the implantation space in the spine. In particular, the invention relates to push-in spinal fusion implants that have height raising capabilities that are utilized once the implant is initially positioned. Such height raising capability may be utilized within the spine anteriorly, posteriorly, or both and to various extents, respectively so as to raise the front, back, or both of the implant by the same or various amounts. More particularly, the invention relates to a push-in implant having upper and lower surfaces of upper and lower members that in a first or insertion position are collapsed relative to one another and in a second or deployed position are adapted to contact the adjacent vertebral bodies.

2. Description of the Related Art

Push-in spinal fusion implants having upper and lower surfaces adapted for placement in contact with adjacent vertebral bodies are known in the related art. Such a push-in spinal fusion implant was invented by Michelson and is disclosed in U.S. Pat. No. 5,776,199, filed Jun. 28, 1988, which is hereby incorporated by reference.

Lordotic or tapered, push-in spinal fusion implants are also known in the art. By way of example, Michelson has invented such implants as disclosed in U.S. Pat. No. 5,609,635, filed Jun. 7, 1995, which is hereby incorporated by reference.

Expandable fusion implants are known in the related art. The first expandable spinal fusion (allowing for the growth of bone from vertebral body to vertebral body through the implant) implant was invented by Michelson and also is disclosed in U.S. Pat. No. 5,776,199 previously incorporated by reference herein.

Lordotic or tapered, spinal fusion implants have the advantage of restoring or enhancing spinal lordosis. Push-in spinal fusion implants offer the advantage of being easily positioned in the implantation space and of having excellent fastening or holding features. Expandable fusion implants offer the advantage of allowing for the placement of a potentially larger implant through a smaller opening in a patient's body. Selective expansion along a single direction, (e.g. vertically only when correctly installed) offers the advantage of increasing the height of the implant and therefore the distraction of the disc space, but without a concomitant increase in the width of the implant.

There exists a need for an artificial interbody spinal fusion implant providing for all of the aforementioned advantages in combination.

SUMMARY OF THE INVENTION

In accordance with the present invention, as embodied and broadly described herein, there is provided an expandable push-in artificial interbody spinal fusion implant with upper and lower surfaces when inserted, for insertion across a disc space between two adjacent vertebral bodies of a human spine. The push-in implant of the present invention includes an upper member having an upper surface adapted for placement toward and into contact with one of the adjacent vertebral bodies and a lower member having a lower surface adapted for placement toward and into contact with the other of the adjacent vertebral bodies. The upper and lower surfaces of the upper and lower members have at least one opening in communication with one another for permitting for the growth of bone from a vertebral body to an adjacent vertebral body through the implant. The upper and lower members are articulated therebetween, preferably proximate one of the proximal ends and the distal ends of the upper and lower members and preferably allow for divergence between the articulating members at the end opposite the articulating end of the implant. The upper and lower members have a first position relative to one another that allows for a collapsed implant height and a second position relative to one another that allows for an increased height. The upper and lower surfaces in the first position of the present invention of one embodiment are generally planar to one another.

As used herein the terms "generally or substantially planar" and "non-arcuate" are intended to describe the upper and lower surfaces of the implant of the present invention as having (1) no curvature, as in a planar surface, (2) slight or mild curvature from the leading end to the trailing end of the implant, and/or (3) slight or mild curvature across the implant width. Slight or mild curvature does not include the curvature associated with the upper and lower surfaces of implants for insertion into a disc space having a circular cross section formed across a spinal disc and into the adjacent vertebral bodies. While the upper and lower surfaces of the present invention may have some curvature, in comparison to an implant having a circular cross section, the curvature is minimal. For implants having a circular cross section such as threaded implants the curvature of the upper and lower surfaces contacting the adjacent vertebral bodies is a radius of half the width of the implant. If there is a curvature to the upper and lower surfaces of the present invention, the curvature is that of a circle much greater than the width of the implant; thus, it has a slight curvature that may correspond to an anatomical curvature of a disc or the surface of the vertebral endplate.

The upper and lower surfaces of the upper and lower members may be either generally parallel or angled to one another when the implant is in the initial insertion position. In another embodiment, the upper and lower surfaces may have a relatively mild convexity in at least one or both directions so as to better conform to the anatomical shape of the disc space or the vertebral endplates. While a substantially parallelepiped shape having a quadrilateral cross section may be generally preferred the leading and trailing ends may be substantially rounded to some advantage.

The height of the implant is at least that of the height of the restored disc space into which it is inserted. The implant is inserted at least in part within the space that was previously occupied by the disc material that was contained between the vertebral bodies.

Preferably, on the exterior of each of the upper and lower surfaces is at least one bone-engaging projection adapted for linear insertion for engaging the adjacent vertebral bodies. The upper and lower members have a leading or distal end, an opposite trailing or proximal end, and a length therebetween. A blocker that is preferably in the form of an expander is preferably located proximate at least one of the ends for holding at least a portion of the upper and lower members apart so as to maintain the increased height of the implant and resist the collapse of the implant to the collapsed implant height. Expansion of the implant preferably increases the implant height only, that is in a plane passing through the mid-longitudinal axis of the implant and the upper and lower members.

The blocker need not be in contact with the upper and lower members when the implant is initially inserted into the implantation space. The blocker may be a block or any type of spacer that is inserted between or otherwise holds apart the articulated upper and lower members after the implant is positioned so as to hold portions of the upper and lower members spaced apart the optimal height and angulation relative to one another. That is, the implant may be expanded with an extrinsic tool and then the expanded portions held apart in the second position by a third body blocker or blockers placed therebetween. Further, a physician may be able to select from a series of blockers having different heights usable with the same implant. The present invention includes expanding the implant with a tool, such as a spreader or a distractor, but is not limited to a scissors type, a rack and gear type, a threaded member type or any other type of particular external expander tool mechanism. Each tool nevertheless preferably engages the upper and the lower implant members to urge the implant apart. Then the blocker may be inserted into contact with the upper and lower members to maintain the implant at an expanded height. The height of the gap created by expanding the implant may be measured so that the appropriately sized blocker or expander may be inserted into contact with the upper and lower members depending upon the amount of distraction of the implant desired by the physician.

In a preferred embodiment, the blocker is in contact with the upper and lower members prior to the implant expansion, and the blocker is itself the expander, which may be operated by an extrinsic tool. By way of example only, the expander may rotate: to increase the height of the implant; in a single direction; more than 40 degrees and less than 140 degrees and more preferably approximately 90 degrees to move from a first insertion position to a second/deployed position; and in a plane perpendicular to the longitudinal axis of the implant to increase the height of the implant. The expander preferably remains in the same perpendicular plane relative to the longitudinal axis of the implant when rotated. In another embodiment the expander may be a member, such as a plate, a rod, or of any other configuration suitable for the intended purpose initially within the interior between the upper and lower members in a collapsed position that is erected to a more erect position when the implant is in the expanded position. The expander can be hollow or solid.

In a preferred embodiment, the expander preferably has means including, but not limited to, an opening, a projection, or a detent adapted to cooperatively engage a tool used to rotate the expander to increase the height of the implant. The opening, projection, or detent is adapted to cooperatively engage a tool that preferably rotates about an axis parallel to the longitudinal axis of the implant to rotate the expander to increase the height of the implant. Rather then having an opening, a projection, a detent, or a central aperture, the expander may have two or more recesses or holes placed on or through the proximal face to engage a tool. In an alternative embodiment of the expander, cutouts may be positioned along a portion of the perimeter of the expander.

The expander is preferably located proximate at least one of the proximal end or the distal end of the upper and lower members. The expander, however, need not be so located. The expander may be spaced away from the end and even permit a hollow portion to exist on both the proximate and distal sides of the expander.

The upper and lower members preferably have an interior surface therebetween and a hollow defined therein with the expander located proximate one of the longitudinal ends of that interior hollow. The hollow between the ends of the upper and lower members is preferably unobstructed by the expander so as to permit growth of bone directly through the hollow unobstructed by the expander from vertebral body to vertebral body through the implant transverse to the longitudinal axis of the implant. The implant may comprise a second and lesser hollow extending at least in part from the expander to the end of the upper and lower members proximate that expander. A preferred expander mechanism includes an expander in combination with cooperating surfaces of the end wall of the implant that guide and support the expander.

Preferred forms of interbody spinal fusion implants have a substantial hollow portion. Certain expandable interbody spinal fusion implants that increase in height only of the related art contain an expansion mechanism passing longitudinally therethrough or an expansion mechanism that is configured for movement of the expansion mechanism from proximate one end of the hollow portion to proximate the other end of the hollow portion, thus requiring the expander to pass through the length of the hollow portion. A preferred embodiment of the present invention overcomes these limitations.

The expander moves the upper and lower surfaces relative to one another from a generally parallel or an angled orientation at a first position to a generally parallel or an angled orientation at a second position or from a first height at each end to a second and greater height at at least one and possibly both ends, including from a first height parallel orientation to a second height parallel orientation. In the first position for initial insertion, when used with an implant inserted from the anterior aspect of the spine the upper and lower surfaces are preferably parallel or angled to be smaller at its leading end. When used with an implant inserted from the posterior aspect of the spine the upper and lower surfaces are preferably parallel or slightly angled to be smaller at its leading end which is then reversed after it is expanded. Each of the upper and lower members may structurally cooperate with a blocker or expander so as to keep it located so as to function for its intended purpose. By way of example, each of the upper and lower members preferably has a track within which the blocker may be captured or the expander rotated. The tracks may be configured to permit the expander to rotate therein and then to move from side to side therewithin. The track of the upper member and the track of the lower member are preferably in the same plane and the plane is preferably perpendicular to the longitudinal axis of the implant.

A preferred expander has a first height in a first or insertion position and a greater second height when rotated or positioned into a second or deployed position to increase the maximum height of the implant from a first maximum height to a second maximum height. By way of example, at least one of the tracks of the upper and lower members preferably has a cooperating surface and the expander has a corresponding cooperating surface that contacts the cooperating surface of the track to orient the expander in a predetermined position. The cooperating surfaces preferably orient the expander within the implant such that the axis of rotation of the expander is parallel with the longitudinal axis of the implant and, more preferably, center the expander within the implant such that the axis of rotation of the expander coincides with the longitudinal axis of the implant. As may be advantageous for the further loading of the implant with fusion-promoting material, the expander may cooperate with the tracking surfaces of the upper and lower members to allow the expander to slide from side-to-side for easier access to the implant interior.

The implant is preferably packed with bone or other fusion-promoting substances prior to expansion of the implant. Expansion of the implant results in a space being formed in the implant interior into which additional fusion promoting substances such as bone may preferably be packed. Rotating the expander within the implant causes a void that can be filled with bone. If the expander is configured to permit side-to-side movement, then packing of additional bone into the implant is facilitated.

When installing a preferred implant from the posterior approach to the spine, the implant is driven from the trailing end and the expander is at the leading end at the anterior aspect of the spine. When expanded, the implant installed from the posterior aspect leaves a void at the leading end of the implant near the anterior aspect of the spine because the leading end of the implant has been made taller, the void preferably being packed with bone. Additionally, the path left behind in the bone filled interior of the implant by the tool used to access the expander through the bone filled interior to position the expander is preferably packed with bone as well.

In a preferred embodiment of the present invention, the expander height change from the first position to the second position corresponds to substantially the same change in height of the implant along at least a portion of the length of the implant. The expander may be configured in different ways. A preferred configuration for a rotational expander includes: a first dimension corresponding to the width of the expander when the implant is initially inserted into the spine and to the height of the rotational expander when the rotational expander is rotated to increase the height of the implant; and a second dimension corresponding to the height of the expander when the implant is initially inserted into the spine and to the width of the expander when the expander is rotated to increase the height of the implant. The first dimension preferably is greater than the second dimension.

The expander may have an upper surface, a lower surface, and side surfaces as defined when the expander is positioned after rotation to increase the height of the implant. As used herein, the term "side surfaces" refers to those portions of the expander that extend from the upper member to the lower member after the expander has been rotated into its second or deployed position to increase the height of the implant. The "upper" and "lower" expander surfaces refer to those portions of the expander that are in contact with the upper and lower members when the implant is in its second or expanded configuration. Each of the upper and lower surfaces of the expander may lie generally in a plane and may be generally parallel to one another. The side surfaces and the upper and lower surfaces may be oriented so as to substantially form a parallelogram, which will typically be in the shape of a rectangle generally.

A preferred expander is in the form of a modified rectangle or rhomboid. The expander generally has a longer dimension and a shorter dimension. When the expander is in a first position, the short dimension spans the distance between the upper and lower members and when the expander is in the second position, the expander's long dimension spans the distance between the upper and lower members.

The expander may have a cross-section with the side surfaces intersecting the upper and the lower surfaces at junctions, which may be two diametrically opposed corners and two diametrically opposed arcs. The two diametrically opposed arcs may be each of the same radius and, preferably, the diagonal or modified hypotenuse "MH" between the opposed arcs has a maximum dimension that generally approximates the distance between the upper and lower surfaces such that, when the expander is rotated from a first insertion position toward a second/deployed position, no substantial over-distraction occurs between the adjacent vertebral bodies as would occur if the height of the implant was increased markedly beyond that obtained in the second/deployed position. The two diametrically opposed corners may form a 90-degree angle. The expander preferably has a fixed shape during movement from a first insertion position to a second/deployed position within the implant.

In a preferred embodiment, a modified hypotenuse or diagonal "MH" is the dimension between the two diametrically opposed arcs that allows for the rotation of the expander from a first position to a second position without substantial over-distraction occurring during this process. The phrase "without substantial over-distraction" is defined as distracting the vertebral bodies in the range of elastic deformation and short of plastic deformation and tissue failure. To avoid any ambiguity regarding the phrase "without over-distraction," this phrase and the individual words contained therein are not being used as they may be in their normal or ordinary use, but are being used as defined in this application only. In the example of this rotational expander, the MH could be identical in length to the height thereby assuring literally no overdistraction. It may be preferred, however, to have the MH just slightly greater in length than the height to insure the stability of the expander in the expanded or second position because this would then require additional force over the stable position to derotate the expander.

In accordance with an embodiment of the present invention, a second expander may be located between the upper and lower members for moving at least a portion of the upper and lower members away from one another to increase the height of the implant as defined by the maximum distance between the upper and lower surfaces proximate that expander. All of the features described herein for the expander may also be applicable to the second expander. Additionally, the second expander may be located proximate an end of the implant opposite the other expander, thereby providing an implant capable of being expanded at both ends of the implant. The increased height of the implant resulting from moving the two expanders may be constant or varied along the length of the implant according to the desired configuration of the implant and the relative dimensions of the individual expanders. A given implant may be adapted to receive or cooperatively engage a series of progressively sized (taller) blockers or expanders to allow the surgeon to make a final height selection at the time of surgery.

In accordance with an embodiment of the present invention, the implant may include an expansion mechanism including the expander and at least one partial wall structure preferably located proximate an implant end that guides and holds the expander in a predetermined position.

The implant may have an overlapping step-cut wall junction between the upper and lower members, which offers as some of its advantages: increasing the lateral rigidity of the implant, holding the implant in the closed first position until expanded, and to the extent desired retaining the fusion-promoting materials within the implant. The wall junction may be either solid or perforated.

One of the upper and lower members preferably has an interior wall extending toward the other of the upper and lower members and, more preferably, has two interior walls extending from each side of the member. The interior walls may be aligned parallel with the longitudinal axis of the implant. The other one of the upper and lower members preferably has an interior-contacting surface adapted to contact or receive the interior longitudinal wall.

By way of example, one of the upper and lower members may have a longitudinally extending interior wall, which is preferably unexposed, extending toward the other of the upper and lower members when the implant is in an initial insertion position. When the implant is in the final expanded or deployed position the implant has a preferred shape such that each of the upper and lower surfaces of the upper and lower members are separated by at least a portion of interior wall, which in this position preferably has an exposed side.

The upper and lower members in certain embodiments are articulated to one another so one of the respective ends of the upper and lower members remain articulated while the other of the respective ends of the upper and lower members are free to move away from one another. In a preferred embodiment, the articulating is achieved without a third member, such as an axle shaft, for example, passing through the implant. The articulating structure preferably is formed into the implant walls themselves, and in a further preference in such a way that the two-implant halves may be articulated when at 90 degrees to each other. The halves then are moved, much like a book closing, toward each other prior to insertion into the implantation space in the spine. Once the upper and lower members are closed from the approximately 90 degrees articulating position, much like closing the leaves of a book, the upper and lower members of the implant are locked together at the articulation so that the members will not disarticulate when in use. Other types of articulation as would be known to one of ordinary skill in the art are within the scope of the present invention.

By way of example, the upper and lower members preferably have a cooperating rotational articulation or pivot point between a proximate one of the proximal end and the distal end of the upper and lower members. The cooperating rotational articulation preferably is proximate one of the proximal end and the distal end of the upper and lower members at an end opposite the expander when only one end is to be expanded. A preferred rotational articulation configuration includes cooperating brackets and projections configured such that articulation therebetween occurs when the upper and lower members are substantially perpendicular to one another. Such a configuration offers the advantage that the brackets and the projections will not disengage one another when articulated for use such as insertion into the spine and subsequent expansion within a range of movement of the upper and lower members resulting from the expander positioning.

At least one and preferably both of the upper and lower members may have a screw hole passing through the trailing end, which preferably is adapted to receive a screw passing through the end of each of the upper and lower members and from the interior of the implant through the upper and lower surfaces, respectively, into each of the adjacent vertebral bodies to anchor the implant. The screw and implant combination stabilize those vertebral bodies relative to each other, prevent undesirable motion at the vertebral body implant interfaces, increase the compressive load at the implant trailing end, prevent rocking; and thus mitigate against excessive peak loads and more uniformly distribute loads imparted to the implant over the length of the implant to the adjacent vertebral bodies.

The trailing end of the implant preferably has a tool-engaging portion, but the implant may be adapted to cooperatively engage a driver at another location or by any means as would be known to one of ordinary skill in the art. This tool-engaging portion is adapted to engage an insertion tool that holds the implant during insertion into position in the spine. The configuration of the tool-engaging portion may be an opening, and more particularly an opening that is along the longitudinal axis of the implant. It is appreciated that the tool-engaging portion need not be an opening. A hole or a blind hole, threaded or otherwise, is preferred in another embodiment. In another preferred embodiment the opening preferably is a threaded slot that functions to cooperatively engage and disengage a tool for use in inserting the implant. In specific embodiments, the leading or trailing end may have wall portions, and/or be adapted to cooperatively engage a cap. Either the end wall portions or a cap may have an opening or openings that may function to hold fusion-promoting materials within the implant and/or, permit vascular access and bone growth therethrough.

For an embodiment of an implant of the present invention having one expander, the main access opening is preferably at the end opposite from the expander. The main opening may be at either the distal or proximal end of the implant. The end of the upper and lower members containing the expander may serve as a secondary access opening.

By way of example, an implant configured for insertion from an anterior approach may be initially packed from the distal or leading end of the implant. The implant is then driven into position. Once the expander is moved into final position and any associated tool for positioning the expander is withdrawn from the expander, any void in the bone packed into the implant interior may be filled. The expander may be moved from side-to-side to pack more bone into the implant. In essence, the side-to-side movement of the expander provides for a secondary access opening for accessing the hollow interior of the implant and for compressively loading it with fusion-promoting substances.

The accompanying drawings, which are incorporated in and constitute a part of this specification, are by way of example only and not limitation, and illustrate several embodiments of the invention, which together with the description, serve to explain the principles of the invention. The scope of the invention is limited only by the scope of the claims as from the present teachings other embodiments of the present invention shall be apparent to those skilled in the art.

BRIEF DESCRIPTION OF THE DRAWINGS

FIG. 1A is a perspective view of an alternative embodiment of a blocker in the form of an expander for use with the spinal fusion implant of FIG. 1;

FIG. 1B is a perspective view of another alternative embodiment of a blocker for use with the spinal fusion implant of FIG. 1;

FIG. 1C is a perspective view of yet another alternative embodiment of a blocker for use with the spinal fusion implant of FIG. 1;

FIG. 5 is a side view of the implant of FIG. 1;

FIG. 6 is a cross-sectional side view along the mid-longitudinal axis of the implant of FIG. 1;

FIG. 21 is a side view of the implant of FIG. 17;

FIG. 22 is a cross-sectional side view along the mid-longitudinal axis of the implant of FIG. 17;

FIG. 23A is a partial cross sectional view of an embodiment of an interlocking wall design shown in the collapsed state for implants of the present invention;

FIG. 23B is a partial cross sectional view of an embodiment of the interlocking wall design of FIG. 23A shown in a partially expanded position for implants of the present invention;

FIG. 24 is a cross-sectional side view of an implantation site formed anteriorly across the disc space between two adjacent vertebral bodies and the implant of FIG. 17 being installed into the implantation site;

FIG. 24A is a side view of an alternative implant having an anatomically shaped upper and lower surface for insertion from the anterior aspect of the spine;

FIG. 25 is a cross-sectional side view of the implantation site formed across the space between two adjacent vertebral bodies and the implant of FIG. 17 installed into the implantation site;

FIG. 32A is a rear perspective view of the end cap of FIG. 32;

FIG. 46 is a top plan view of the lower member of the implant of FIG. 42;

FIG. 47 is a side view in partial cross section of a cap for use with the implant of FIG. 42;

FIG. 48 is a top plan view of a preferred embodiment of a bone screw for use with the implant of FIG. 42;

FIG. 49 is a side elevation view of the screw of FIG. 48;

DESCRIPTION OF THE PREFERRED EMBODIMENTS

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings.

Figure 55:
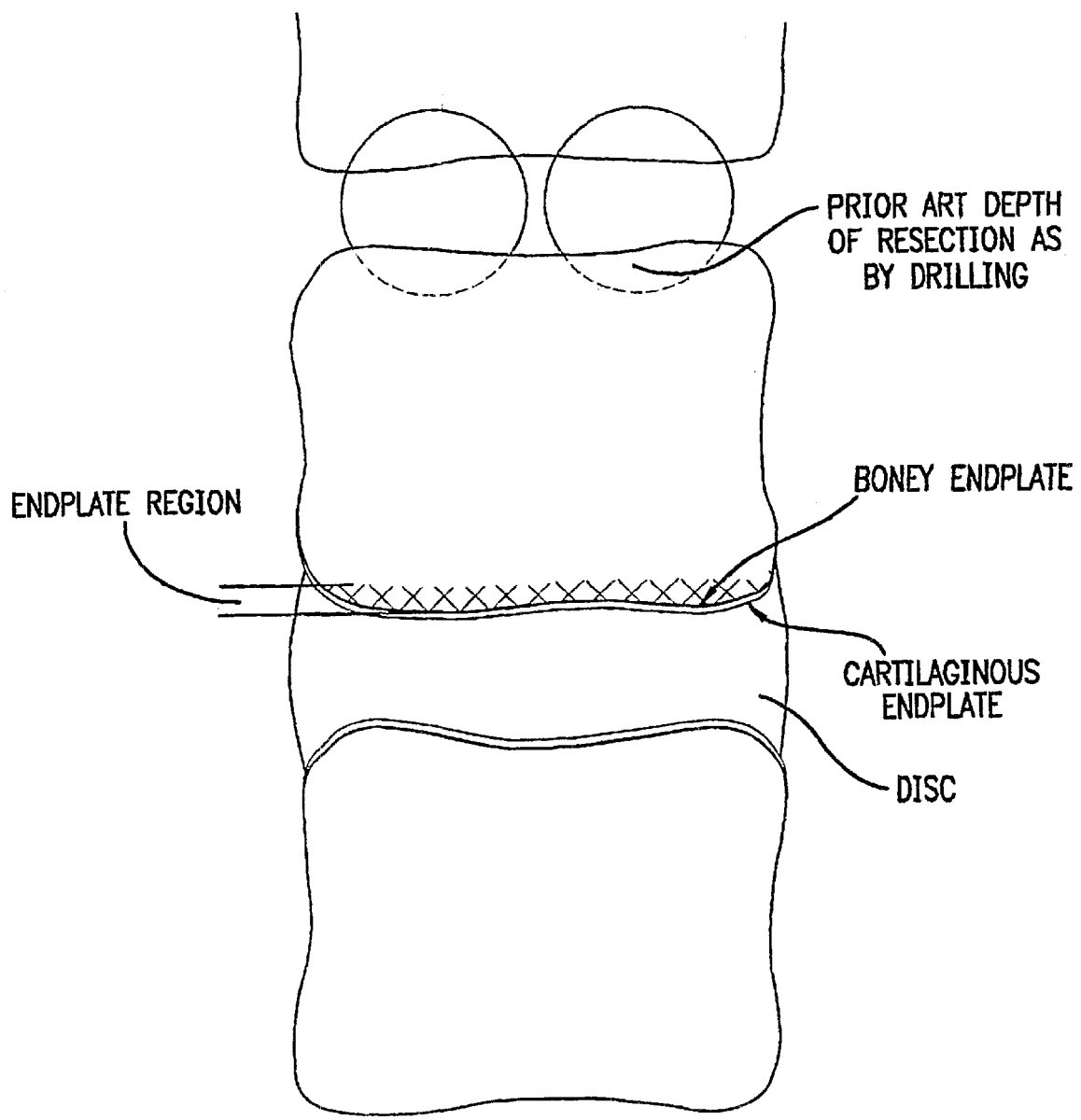
FIG. 55 is a front elevation view of two disc levels of the lumbar spine showing the prior art depth of resection resulting from drilling through the bony endplate region of adjacent vertebral bodies and showing the endplate region on a vertebral body.

Human vertebral bodies have a hard outer shell of compacted dense cancellous bone (sometimes referred to as the cortex) and a relatively softer, inner mass of cancellous bone. Just below the cortex adjacent the disc is a region of bone referred to herein as the "subchondral zone". As best shown in FIG. 55, the outer shell of compact bone (the bony endplate) adjacent to the spinal disc and cartilaginous endplate and the underlying subchondral zone are together herein referred to as the bony "end plate region" and, for the purposes of this application, is hereby so defined. In the lumber spine the bony endplate is generally 2 mm deep. By way of example, prior art threaded implants requiring approximately a 3 mm drill depth into the vertebral body will have threads of approximately 1 mm or more resulting in a total depth of penetration into the vertebral body of 4 mm or more. The implant of the present invention and associated method permits the implant to penetrate into the vertebral bodies to a depth of less than 3 mm or not to penetrate into the vertebral bodies.

Shown in FIGS. 1–6 and 10–16, in accordance with the present invention, as embodied and broadly described herein, is one embodiment of an expandable push-in artificial interbody spinal fusion implant 100 for posterior insertion across a disc space D between two adjacent vertebral bodies V of a human spine. Push-in implant 100 of the present invention includes an upper member 102 having an upper surface 104 adapted for placement toward and into contact with the upper of the adjacent vertebral bodies V and a lower member 106 having a lower surface 108 adapted for placement toward and into contact with the lower of the adjacent vertebral bodies V. Upper and lower surfaces 104, 108 of upper and lower members 102, 106 have at least one opening 110, 112 in communication with one another for permitting for the growth of bone from vertebral body V to adjacent vertebral body V through implant 100. Upper and lower members 102, 106 are articulated therebetween at an adjacent one of the proximal ends and the distal ends of upper and lower members 102, 106 and allow for rotation between the articulating members at the end opposite the articulating end of implant 100. Upper and lower members 102, 106 have a first position relative to one another that allows for a collapsed implant height and a second position relative to one another that allows for an increased height. Upper and lower surfaces 104, 108 of upper and lower members 102, 106 in the first position of the present invention are parallel to one another. On an exterior 120 of each of opposed upper and lower surfaces 104, 108 of upper and lower members 102, 106 is at least one bone-engaging projection 118 adapted for linear insertion, which in one preferred embodiment is a ratchet. Alternatively, bone-engaging projection 118 can be a surface roughening, knurling, or any other configuration suitable for the intended purpose. While a specialized form of a blocker 121 is described in significant detail below with reference to expander 122, blocker 121 need not be in contact with upper and lower members 102, 106 when implant 100 is initially inserted into the implantation space. Blocker 121 may be a block or any type of spacer that is inserted between the articulated upper and lower members 102, 106 after implant 100 is positioned so as to hold portions of the upper and lower members 102, 106 spaced apart the optimal height and angulation relative to one another. That is the implant may be expanded with an extrinsic tool and then the expanded portions held apart in the second position by a third body blocker placed therebetween. Further, a physician may be able to select from a series of blockers having different heights usable with the same implant. The present invention includes expanding the implant with a tool, such as a spreader or a distractor but is not limited to a scissors type, a rack and gear type, a threaded member type or any other specific type of movement mechanism. Each tool nevertheless preferably engages upper and lower implant members 102, 106 to urge them apart. Blocker 121 is then inserted into contact with upper and lower members 102, 106 to maintain implant 100 at an expanded height. The height of the gap created by expanding implant 100 may be measured so that the appropriately sized blocker 121 or specialized blocker, expander 122, may be inserted in implant 100 depending upon the amount of distraction of implant 100 desired by the surgeon.

Blocker 121 that is preferably in the form of expander 122 is located proximate at least one of the ends of the implant upper and lower members 102, 106 and holds at least a portion of upper and lower members 102, 106 apart so as to maintain the increased height of implant 100 and resist the collapse of implant 100 to the collapsed implant height. Expander 122 in the present embodiment increases the implant height as measured in a plane passing through the mid-longitudinal axis of implant 100 and upper and lower members 102, 106 during positioning of expander 122 and as may be desirable is capable of selectively increasing the height of the implant only.

Figure 1:
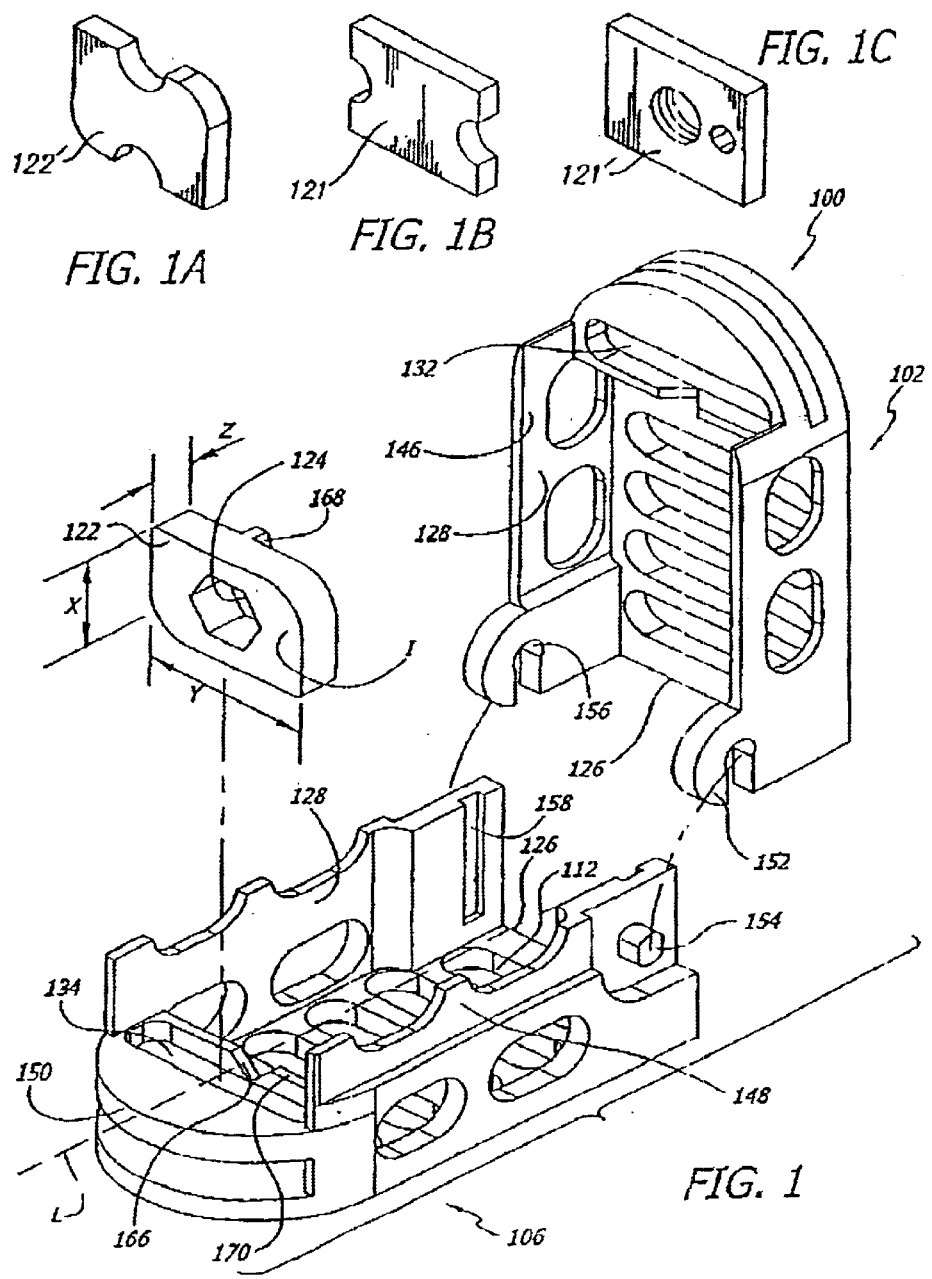
FIG. 1 is an exploded perspective view of a spinal fusion implant of one embodiment of the present invention.
Figure 2:
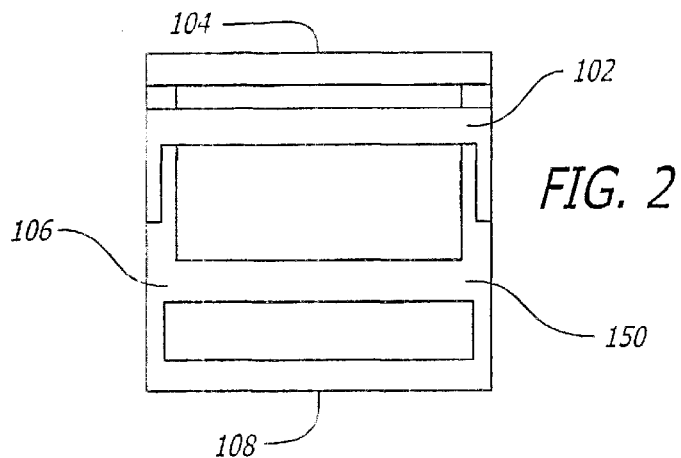
FIG. 2 is a leading end plan view of the implant of FIG. 1.
Figure 3:
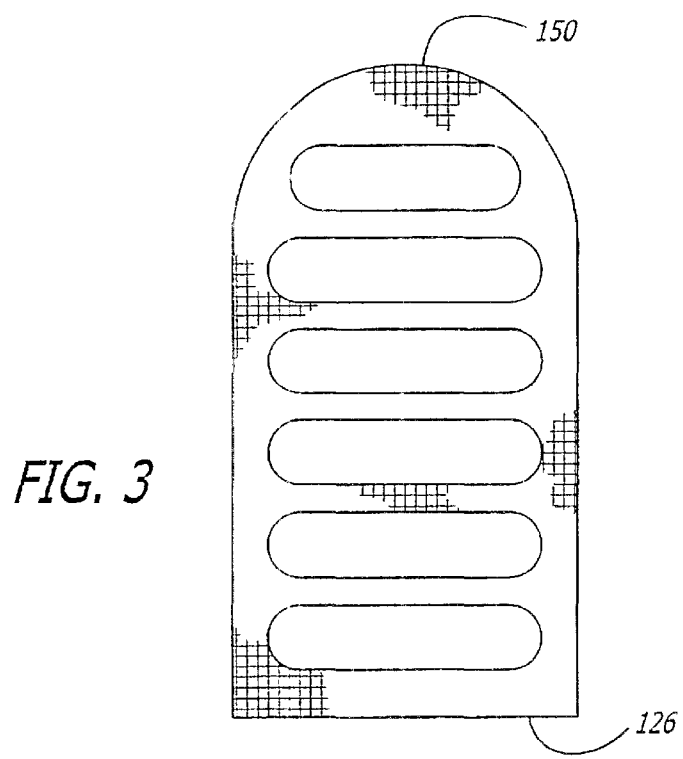
FIG. 3 is a top view of the implant of FIG. 1.
Figure 4:
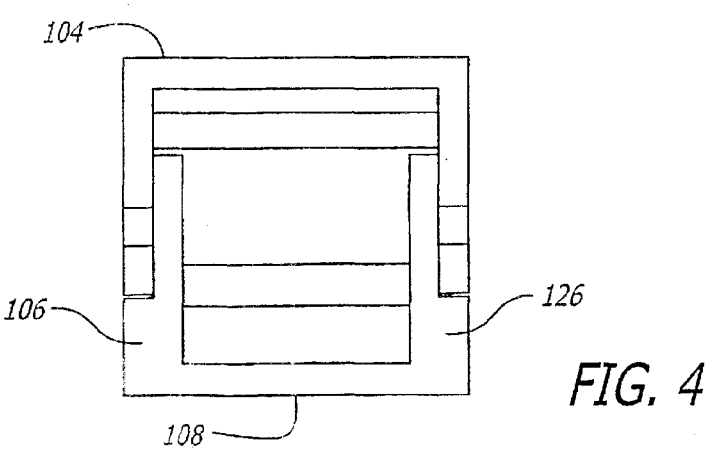
FIG. 4 is a trailing end view of the implant of FIG. 1.
Figure 7:
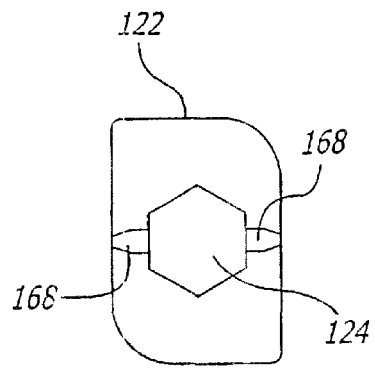
FIG. 7 is front view of one embodiment of an expander of the present invention.
Figure 8:
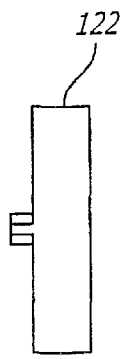
FIG. 8 is a side elevation view of the expander of FIG. 7.
Figure 10:
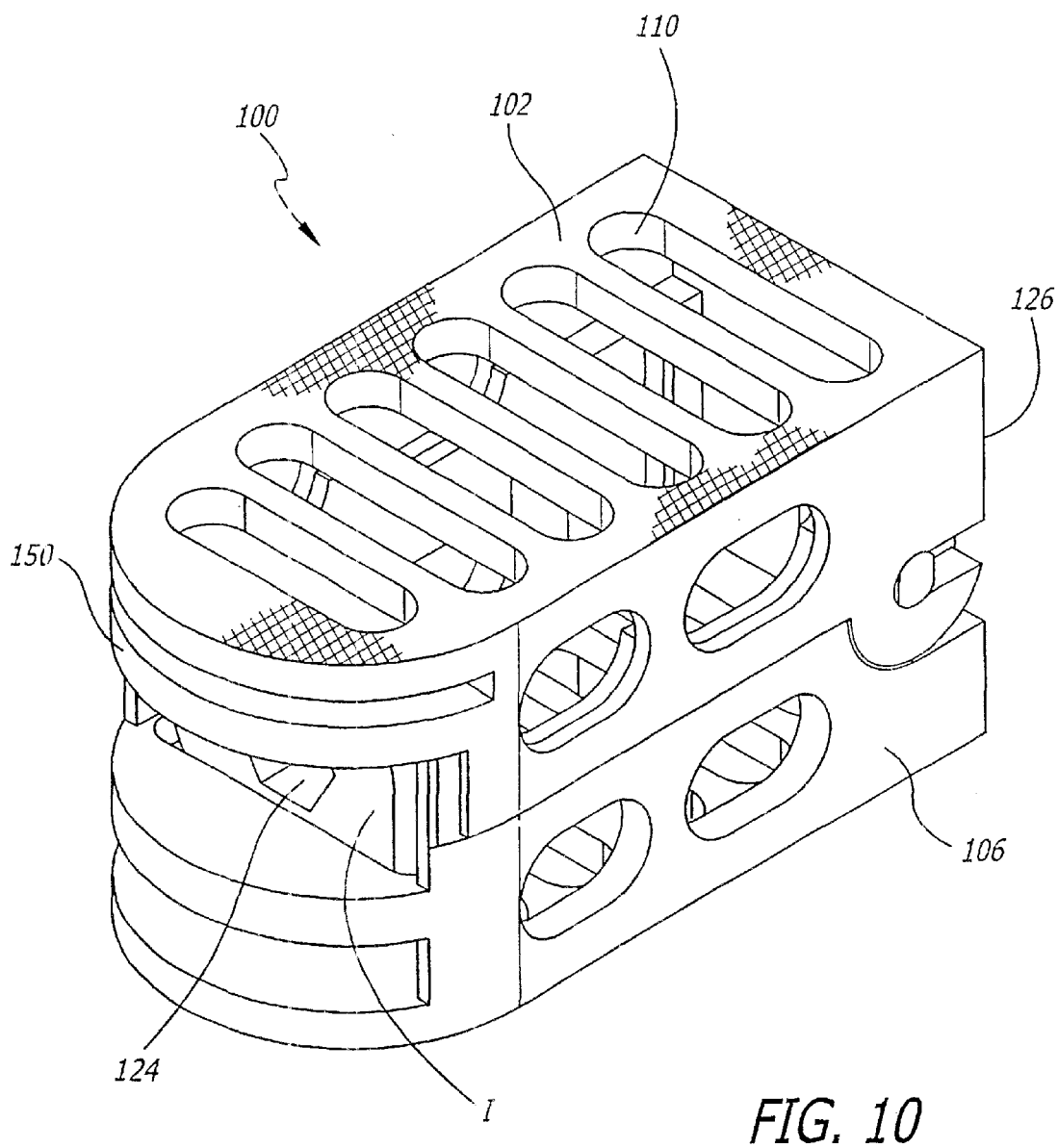
FIG. 10 is a leading end perspective view of the implant of FIG. 1.
Figure 16:
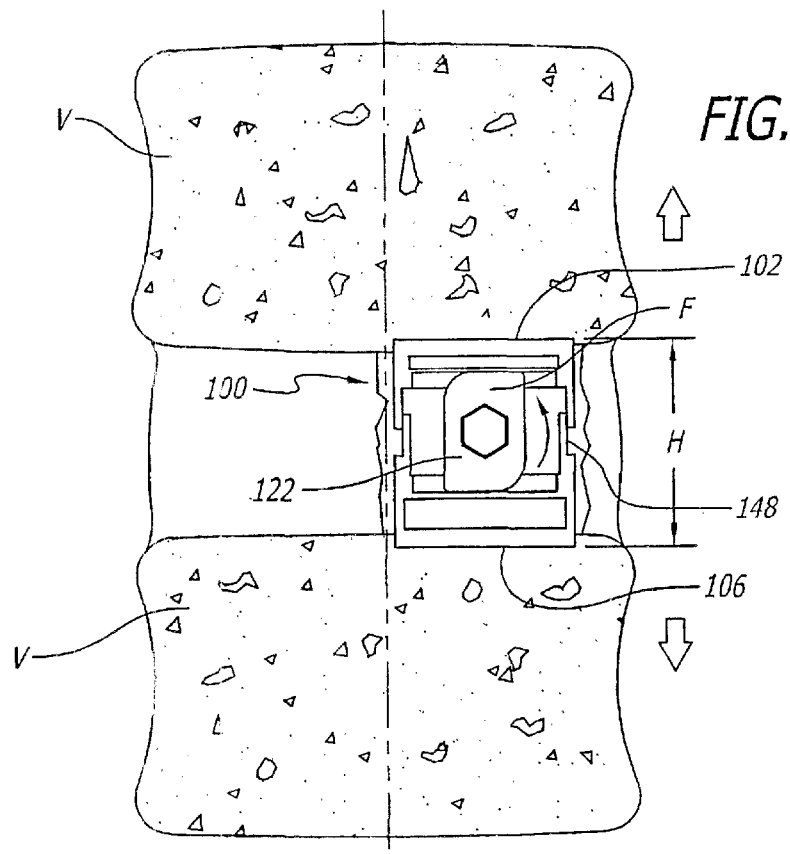
FIG. 16 is a cross-section leading end view of the implant of FIG. 1 implanted between adjacent vertebral bodies so as to show the expander in the final deployed position.

Expander 122 in the present embodiment is adapted to rotate in a single direction approximately 90 degrees to move from an initial (first) insertion position I, as best shown in FIGS. 1 and 10, to a final (second) deployed or expanded position F, as best shown in FIG. 16, to increase the maximum height H of implant 100. Expander 122 preferably rotates in a plane perpendicular to the longitudinal axis L of implant 100 to increase the maximum height H of implant 100. During rotation, expander 122 remains in the same perpendicular plane relative to the longitudinal axis L of the implant. It is appreciated that an expander within the scope of the present invention may be designed to: rotate in either direction or both directions; rotate more than 40 degrees and less than 140 degrees; rotate more or less than 90 degrees; or rotate in a plane other than perpendicular.

Expander 122 has an opening 124 adapted to cooperatively engage a tool (not shown) used to rotate expander 122 to increase height H of implant 100. Opening 124 is adapted to cooperatively engage a tool that preferably rotates about an axis parallel to the longitudinal axis L of implant 100 to rotate expander 122 to increase height H of implant 100. Opening 124 also may be used as a passageway to pass fusion-promoting substances through expander 122 and into implant 100. It is appreciated that the expander may also include a projection, a detent, or any other configuration in place of or in addition to an opening so as to cooperatively engage a tool to move the expander.

In an alternative embodiment an expander 1221 could have cutouts along any portion of its perimeter not involved in the actual rotation as shown in FIG. 1A. In another alternative embodiment, a blocker 121 having cutouts along a portion of its perimeter can be positioned into the implant as shown in FIG. 1B. The cutouts can be used to engage a raised area within the implant to lock blocker 121 or expander 122' into position or be used by the surgeon to grasp blocker 121 with a tool that cooperatively engages the cutouts to facilitate inserting blocker 121 into the implant. Rather then having an opening, a projection, a detent, or a central aperture, a blocker 121' alternatively could have two or more recesses or holes placed on or through the proximal face to engage a tool as shown in FIG. 1C.

As shown in FIGS. 1, 10 and 16, in one preferred embodiment of the present invention for posterior insertion, expander 122 is located proximate the leading end 150 of upper and lower members 102, 106. In another embodiment shown in FIGS. 17–28 for anterior insertion, expanders 222 used in implant 200 are located proximate each of the trailing end 226 and leading end 250. An alternative embodiment of the present invention for anterior insertion shown in FIGS. 29–31 has an expander 322 located proximate trailing end 326 only of implant 300. Implant 100 preferably has an interior surface 128 and a hollow 130 defined therein. Expander 122 of the present embodiment is located proximate interior surface 128 and more particularly proximate interior surface 128 at leading end 150 of upper and lower members 102, 106. As is preferred, hollow 130 between the ends is unobstructed by expander 122 so as to allow for the unimpeded loading of the interior of the implant with the desired fusion-promoting substances; thus, loading the implant is easy. Further, this preferred configuration of implant 100 makes available all of the volume of the hollow to contain fusion-promoting substances and so as to permit for the growth of bone directly through the hollow unobstructed by the expander to adjacent vertebral bodies V. Unobstructed hollow 130 further allows for packing implant 100 with fusion-promoting substances. It is appreciated that depending on the intended results, the expander also may be located at distal end 126 or leading end 150 of upper and lower members 102, 106 or anywhere else within the implant. The unobstructed hollow preferably has no mechanism extending along the longitudinal axis of the implant when finally deployed and the mechanism that moves the implant from a first position to a second position preferably does not move expander 122 longitudinally through the hollow portion. The expander may work by pivoting on a surface in contact with an interior wall portion of at least one of the upper and lower members 102, 106. Moreover, multiple expanders may be used in contact with upper and lower members 102, 106 at any location within implant 100.

An alternative embodiment of an expander used with the present invention includes an expander having an external thread that cooperates with converging threaded portions of the upper and lower members 102, 106 to expand the implant as the expander is rotated into position. Another alternative embodiment of an expander includes an expander having a cam configuration to expand the implant upon rotation.

The mechanism or tool used to move the expander is not part of the implant itself as the mechanism or tool is removed from the implant upon moving the expander, e.g. such as to rotate it into place and thus expand the implant to the final expanded position.

Figure 11:
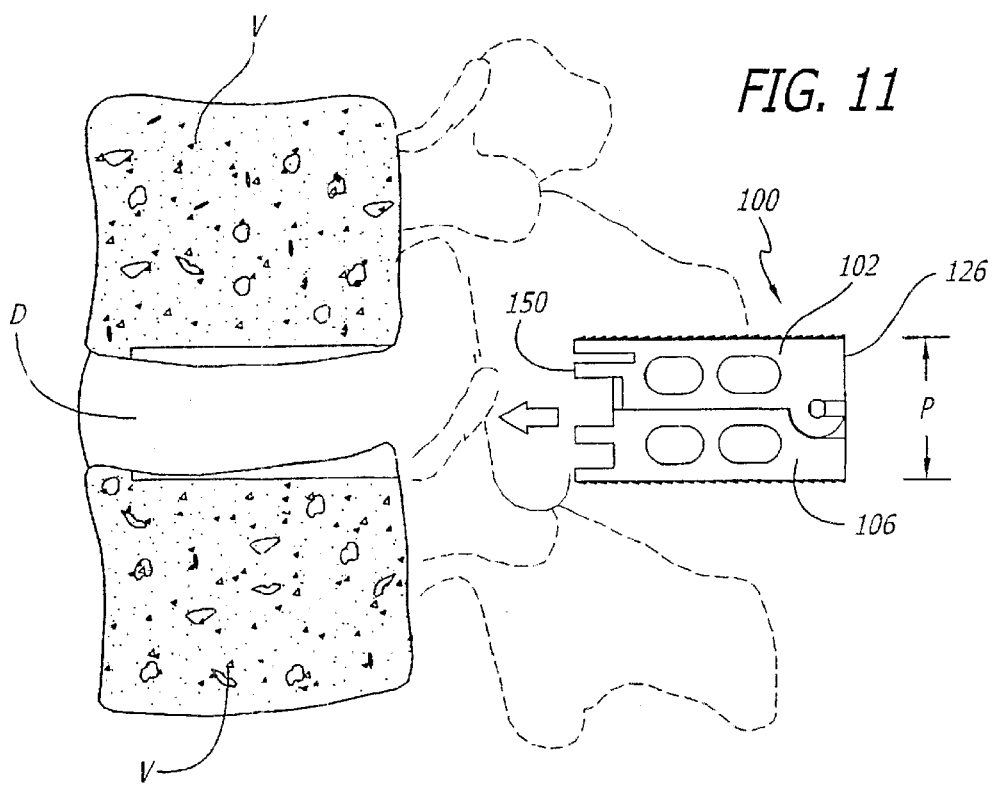
FIG. 11 is a side view of the implant of FIG. 1 being inserted from a generally posterior approach to the spine into an implantation site formed across a disc space and two adjacent vertebral bodies of the spine shown in partial cross-section.
Figure 12:
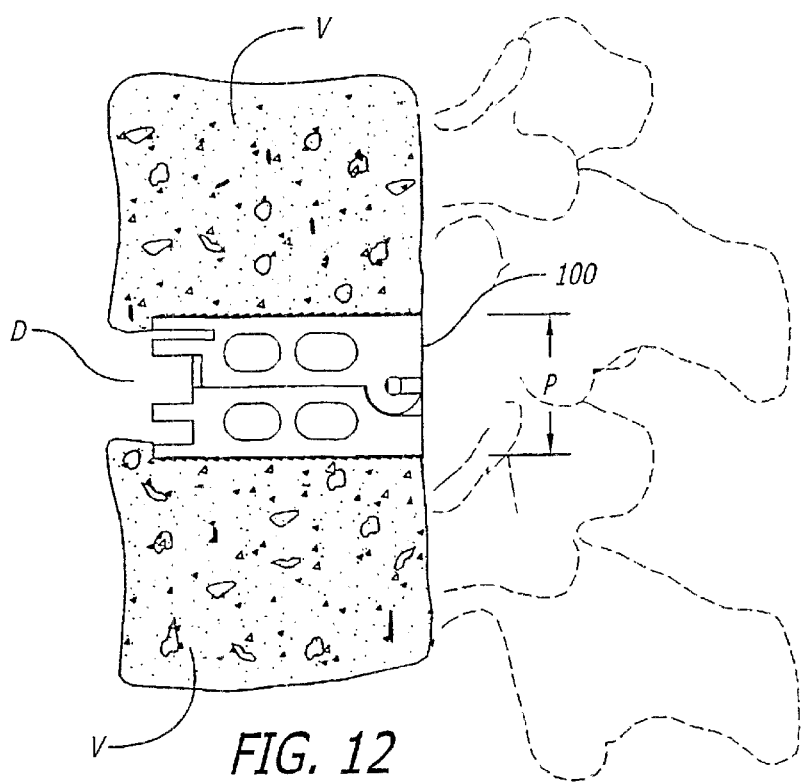
FIG. 12 is a side view of the implant of FIG. 11 inserted in an implantation site formed across the disc space and two adjacent vertebral bodies of the spine.
Figure 13:
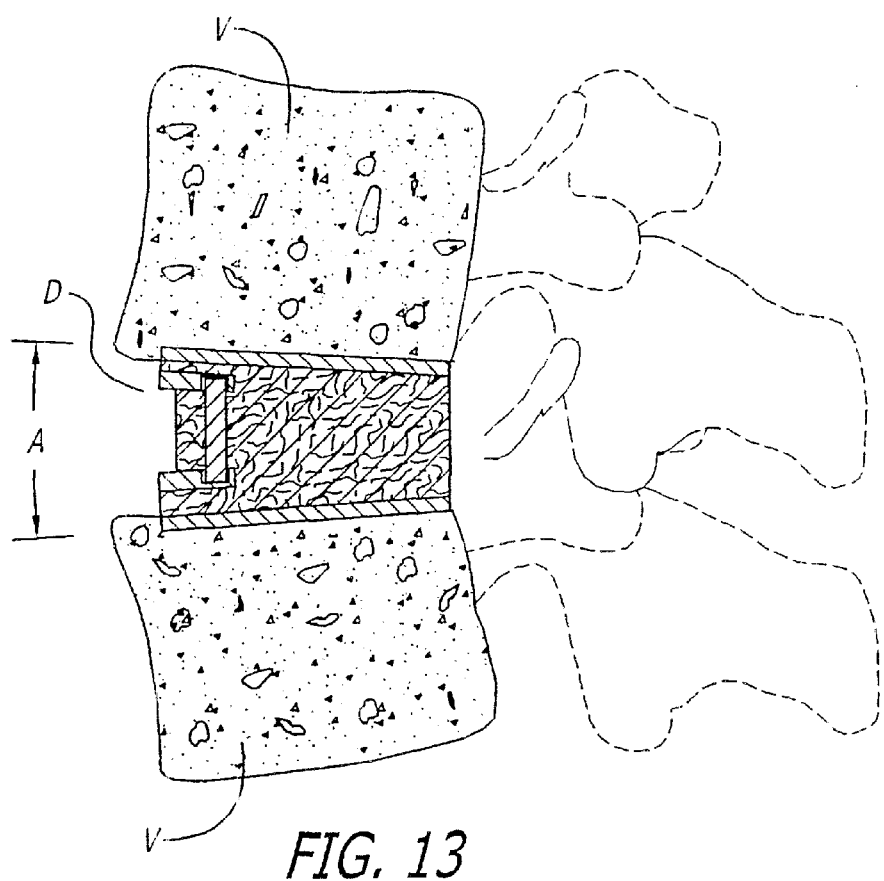
FIG. 13 is a cross-sectional side view of the implant of FIG. 11 with the implant in an expanded position inserted in an implantation site formed across the disc space and two adjacent vertebral bodies of the spine.

Expander 122 of the present embodiment moves upper and lower surfaces 104, 108 of upper and lower members 102, 106 from a parallel orientation P, as shown in FIGS. 11 and 12 where implant 100 is in a first position, to an angled orientation A, as shown in FIG. 13 where implant 100 is in a second position. It is appreciated that the expander also may move the upper and lower surfaces of the upper and lower members from a first height at each end to a second and greater height at each end.

Figure 14:
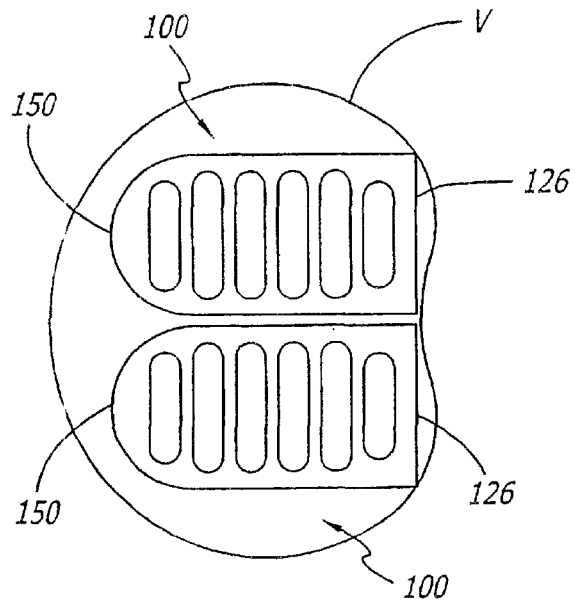
FIG. 14 is a top view of two implants of FIG. 1 implanted in a final position upon the lower vertebral body of an implantation site formed posteriorly across a disc space.
Figure 15:
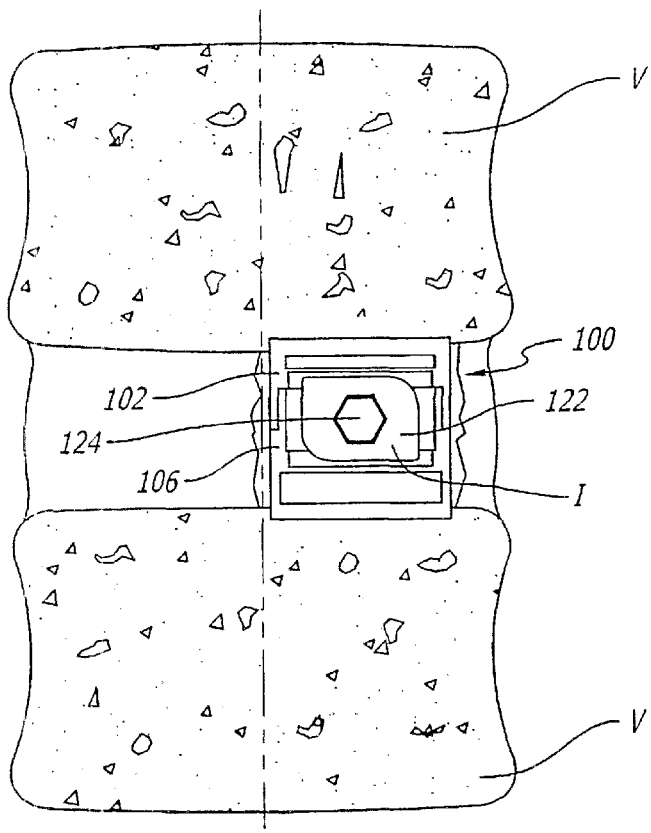
FIG. 15 is a cross-section leading end view of the implant of FIG. 1 implanted between adjacent vertebral bodies so as to show the expander in the initial insertion position.

FIG. 14 is a top view of two implants 100 implanted in a final position upon a lower vertebral body of an implantation site formed posteriorly across a disc. In an alternative embodiment the corners of the trailing end may be chamfered, radiused, or otherwise relieved to ensure that they do not protrude beyond the vertebral bodies and the leading end may be asymmetrical or otherwise shaped as may be beneficial for the intended purpose.

Similar implants may be used in the reverse direction, from anterior to posterior by moving the pivot to the leading end and having the expander at the trailing end. Thus, the implant will get taller at its trailing end instead of its leading end. This smaller width implant design can be used to do an anterior approach spinal fusion where the surgeon wants to put in two implants instead of one large implant as when the surgery is to be preformed laproscopically.

In this embodiment, each of upper and lower members 102, 106 structurally cooperate with expander 122 so as to keep it located so as to function for its intended purpose. Each of upper and lower members 102, 106 of the implant of FIG. 1 has a track 132, 134 within which expander 122 rotates. As best shown in FIGS. 1 13, 15, and 16 track 132, 134 is configured to permit expander 122 to rotate therein and then to move from side to side within track 132, 134. Track 132 of upper member 102 and track 134 of lower member 106 are in the same plane and the plane is perpendicular to the longitudinal axis of implant 100. It is appreciated that the track of the upper and lower members may be in different planes. Such a track design may be used with an expander with a step in it or with offset tabs to engage tracks in different planes than one another. As with the expander, the tracks also may be at various angles to the longitudinal axis of the implant including parallel with the longitudinal axis of the implant. Tracks 132, 134 include sides 170 having cooperating surface 166 and expander 122 has corresponding cooperating surface 168 used to orient expander 122 in a predetermined location. Cooperating surface 166 of side 170 is a detent and corresponding cooperating surface 168 of expander 122 is a projection. The projection preferably projects toward expander 122 in a direction parallel to the longitudinal axis of implant 100. The detent and the projection preferably center expander 122 within implant 100 such that the axis of rotation of expander 122 coincides with the longitudinal axis of implant 100.

Other means for respectively engaging the implants and the expander position thereof are anticipated and within the scope of the present invention.

Figure 9:
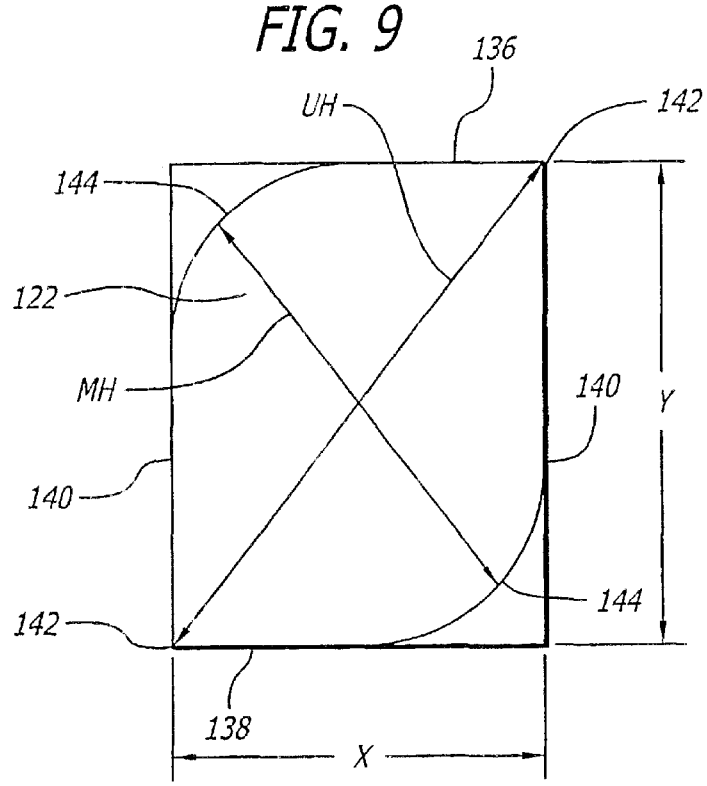
FIG. 9 is a schematic representation of a geometric configuration of a cross-section of an expander in accordance with one embodiment of the present invention.

In rotating the expander, the longer dimension of the expander is substituted for the lesser dimension of the expander thus correspondingly increasing the maximum height of the implant from the first to the second position. As best shown in FIG. 9, the schematic representation of a geometric configuration of a cross-section of an expander 122 in accordance with one embodiment of the present invention, includes: a first dimension X corresponding to the height of expander 122 when implant 100 is initially inserted into the spine and to the width of expander 122 when expander 122 is rotated to increase height H of implant 100; and a second dimension Y corresponding to the width of expander 122 when implant 100 is initially inserted into the spine and to the height of expander 122 when expander 122 is rotated to increase height H of implant 100. Second dimension Y is greater than first dimension X. Expander 122 has an upper surface 136, a lower surface 138, and side surfaces 140 as defined when expander 122 is positioned after rotation to increase height H of implant 100. As used herein, the term "side surfaces" refers to those portions of expander 122 that extend from upper member 102 to lower members 106 after expander 122 has been rotated into its final deployed, or second position to increase the height H of implant 100. The "upper" and "lower" surfaces refer to those portions of expander 122 that are in contact with upper and lower members 102, 106 when implant 100 is in its second position and configuration and is fully expanded.

A preferred expander 122 is in the form of a modified rectangle or rhomboid. The expander generally has a longer dimension Y and a shorter dimension X. When the expander is inserted into a first position, the short dimension X spans the distance between upper member 102 to lower member 106 and when expander 122 is in the second position, the longer dimension Y of expander 122 spans the distance between upper and lower members 102, 106.

Expander 122 in one embodiment of the present embodiment has a cross-section with side surfaces 140 intersecting upper and lower surfaces 136, 138 at two junctions which may be diametrically opposed corners 142 and two diametrically opposed arcs 144. Arcs 144 are preferably each of the same radius and the modified hypotenuse MH between opposed arcs 144 generally approximates the distance between upper and lower surfaces 136, 138 such that, when expander 122 is rotated from an initial insertion position toward a final deployed position, no substantial over-distraction occurs between adjacent vertebral bodies V. The modified hypotenuse MH of this embodiment of the present invention may be equal, slightly less than, or slightly greater than dimension Y of expander 122. Having the modified hypotenuse MH be slightly greater than the dimension Y offers the advantage of having expander 122 stabilized by an over-center position, such that more energy would be required to derotate the expander than for it to remain in the deployed or second position. By "without substantial over-distraction" what is meant is that the modified hypotenuse MH length is closer to the expander dimension Y than to the unmodified hypotenuse UH; and is selected to allow the implant to preferably operate in the range of elastic deformation of the tissues about the operated disc space. Corners 142 may form, but not necessarily, a 90-degree angle and have an unmodified hypotenuse dimension UH.

By way of example, consider one embodiment of expandable implant 100 of the present invention having an optimum expanded height of 18 mm for a given implantation space. Any implant bigger than 18 mm should not be used in this implantation space because during expansion of the implant, its height would move through the range of elastic deformation of the surrounding tissues and after that the implant would crush the vertebral bone or tear ligaments. Inserting an expander such that when the implant is fully expanded allows the implant to be 18 mm would be ideal. It may be that an implant having a 17.5 mm expanded height for this implantation space is nearly as good, but a 16 mm expanded height may be too short to fit tightly within the implantation space. Using a preferred rectangular expander without any modification to the hypotenuse that is adapted to expand the implant to the optimum 18 mm final height would require the expander to have a hypotenuse causing the implant to exceed the 18 mm expanded height temporarily during rotation of the expander. So turning the expander without a modified hypotenuse would break the vertebrae or tear the ligaments. In reverse, if one could not expand the implant to more than 18 mm without causing damage to the spine, then an implant selected to have an expander having a full unmodified hypotenuse so as to upon rotation temporarily cause the implant height to be 18 mm would in the finally expanded position allow the implant height to collapse such that there would be insufficient height for the implant to adequately distract the implantation space. Generally, the modified hypotenuse of the expander is closer in length to dimension Y of the expander than to the unmodified hypotenuse.

As best shown in FIG. 1 in this particular embodiment, expander 122 has a depth dimension Z that is less than that of first and second dimensions Y, X. Expander 122 of the present embodiment has a fixed shape during movement from initial insertion position I to final deployed position F within implant 100.

While modified hypotenuse MH is illustrated as being between arcs 144 in this preferred embodiment, the configuration of expander 122 to form modified hypotenuse MH can take many forms, such that those junctions are relieved so as to have the desired lesser dimension therebetween, including arcs, chamfers, a series of angled surfaces, or any other shape so long as the modified hypotenuse MH is sufficiently reduced in dimension to function for the intended purpose according to the present teaching.

An embodiment of the present invention where modified hypotenuse MH is slightly greater than height Y offers the advantage of an over-center effect that locks expander 122 into place. In this instance, once expander 122 rotates past the diagonal of the modified hypotenuse MH, more force would be required to rotate it back from the final deployed position to its insertion position than in an embodiment where modified hypotenuse MH is equal to or less than height Y. Preferably, expander 122 offers a surgeon multiple sensory advantages including: the tactile feel of expander 122 going over center and locking into place; the visual of the handle of a tool rotating expander 122 such that the tool handle goes from perpendicular to parallel, the reverse, or other, to the disc space into place; and auditory from the sound of expander 122 snapping into place.

Each of upper and lower surfaces 136, 138 of expander 122 of the present embodiment lie generally in a plane and are generally parallel to one another. For any implant it is anticipated that a physician may be able to select from a series of blockers or expanders allowing for varying the increase in the implant height. Side surfaces 140 and upper and lower surfaces 136, 138 are oriented so as to substantially form a parallelogram. Any of a number of configurations for the expander for increasing the height of the implant is possible, based on the teachings of the present application and such configurations as would be known to one of skill in the art are anticipated within the scope of the present invention.

The implant may preferably have an overlapping step-cut wall junction between upper and power members 102, 106 which offers the advantage of increasing the lateral rigidity of implant 100 holding the implant in the closed first position until expanded, and to the extent desired retaining the fusion-promoting materials within. The wall junction may be either solid or perforated. As best shown in FIG. 1, upper member 102 in one embodiment of the preferred invention has interior walls 146 extending from each side of upper surface 104 toward lower member 106. Interior wall 146 is aligned parallel to longitudinal axis L of implant 100. Lower member 106 has an interior-contacting surface 148 adapted to contact or receive interior wall 146.

In a preferred embodiment, upper and lower members 102, 106 are articulated to one another so one of the respective ends of upper and lower members 102, 106 remain articulated while the other of the respective ends of upper and lower members 102, 106 are free to move away from one another. In a preferred embodiment the articulating means is achieved without a third member such as an axle shaft passing through the implant. The articulating means preferably is formed into the implant walls themselves in such a way that the two implant halves may be articulated when the halves are at 90 degrees to each other and then the halves are moved toward each other for insertion into the implantation space in the spine. The two halves are closed much like the cover of a book. The halves are locked together such that disarticulation will not occur when the implant is assembled for use. Any of a number of ways of articulating or joining upper and lower members 102, 106 is possible.

As best shown in FIG. 1 in this embodiment, upper and lower members 102, 106 of the present embodiment have a pivot point between adjacent distal ends 126 of upper and lower members 102, 106. The pivot point in the present embodiment is at the end of implant 100 opposite expander 122. The pivot point of the present embodiment operates as a hinge or axle 152 but is formed out of the walls themselves so as to preferably not intrude into the implant interior or hollow or to block access thereto. Hinge 152 includes a projection 154 extending radially from each side of interior-contacting surface 148 of lower member 106 and a slotted bracket 156 extending from each side of upper member 102 for engaging projection 154. Brackets 156 and projections 154 are configured such that engagement occurs when upper and lower members 102, 106 are substantially perpendicular to one another. Brackets 156 and projections 154 are configured so as not to disengage within a range of movement of upper and lower members 102, 106 that would occur when the implant is in use either during insertion or resulting from the expansion in height of implant 100.

As best shown in FIGS. 10–12 and 15, interior-contacting surface 148 of lower member 108 of the present embodiment is unexposed when implant 100 is in initial insertion position I. As shown in FIG. 16, when implant 100 is in the expanded position F, implant 100 has a shape such that each of upper and lower members 102, 106 are separated by at least a portion of interior-contacting surface 148, which in this position has an exposed side. The exposed side of the present embodiment is smooth and flat.

A slot 158 on implant 100 is adapted to receive in a lockable way a driver and to thereafter, if so desired by the surgeon, a cap that snaps into slot 158. As discussed above, implant 100 has a leading end 150 and a trailing end 126. One of the ends preferably has a tool-engaging portion. This tool-engaging portion is adapted to engage an insertion tool that holds implant 100 during insertion into position into the spine. The tool-engaging configuration may be an opening, and more particularly an opening that is along the longitudinal axis of the implant. Of course, the tool-engaging portion need not be an opening. A hole or a blind hole, threaded or otherwise, is preferred in another embodiment. In another preferred embodiment the opening preferably is a threaded slot that functions to cooperatively engage and disengage a tool for use in inserting implant 100.

A cap having an exterior surface and an interior surface may be used to close trailing end 126 of implant 100. The interior surface of the cap may have spaced slots about its circumference to facilitate a snap fit between the cap and the implant 100. The cap and implant 100 can of course be adapted for either or both ends of implant 100. Further, the cap may be solid or perforate and made of a surgical quality plastic that may be resorbable or of any other suitable material.

For a posterior approach implant, it may be desirable to have a cap on the trailing end. The trailing end of the implant in a posterior approach implant has direct exposure to the spinal canal where the spinal cord and nerve roots are located. A cap on a posterior approach implant may be for the purpose of sealing off the spinal canal from the fusion-promoting substances contained in the hollow interior of the implant so that no bone grows into the canal. Further, the present invention implant may be used in combination with chemical substances and/or compounds applied at the trailing end of the implant to inhibit scar formation, and the cap may be of benefit in shielding the fusion-promoting substances contained in the implant from these scar formation inhibiting chemicals and compounds. It may also be for the purposes identified herein used in association with the leading end cap of an anterior approach implant.

An anterior approach implant may have a leading end, trailing end, or both ends that are adapted to engage a cap. One of the purposes for that cap includes restricting the passage of fusion-promoting substances so that they remain loaded within the implant. Another purpose of the cap may be to add structural support to the implant. The cap may be solid or it may have openings therethrough. Any such openings could allow for the loaded material to stay within the implant while providing for vascular access to allow for the ingrowth of blood vessels and the growth of bone through the end of the implant.

Shown in FIGS. 17–28, in accordance with the present invention, as embodied and broadly described herein, is an embodiment of an expandable push-in artificial interbody spinal fusion implant 200 for anterior insertion across a disc space D between two adjacent vertebral bodies V of a human spine. Push-in implant 200 of the present invention includes an upper member 202 having an upper surface 204 adapted for placement toward and in contact with the upper of the adjacent vertebral bodies V and a lower member 206 having a lower surface 208 adapted for placement toward and in contact with the lower of the adjacent vertebral bodies V. Implant 200 in FIGS. 24 through 28 is shown being implanted into the spine from the anterior aspect with expanders 222 on the distal end 226 and leading end 250 of implant 200. While anterior and posterior aspect approaches have been illustrated herein, the present invention is not limited to these illustrated approaches. In particular, but not limited thereto, the push-in implant of the present invention also may be used in push-in implants for insertion from the translateral aspect of the spine as disclosed by Michelson in U.S. Pat. No. 5,860,973, which is incorporated herein by reference.

FIG. 24A is a side view of an alternative implant having an anatomically shaped upper and lower surface for insertion from the anterior aspect of the spine. The anatomical curvature may correspond to that of a disc or the surface of the vertebral endplate. In another embodiment, the upper and lower surfaces may have a relatively mild convexity in both directions, that is from leading to trailing end as well as side-to-side so as to better conform to the anatomical shape of the disc space or the vertebral endplates.

Figure 26:
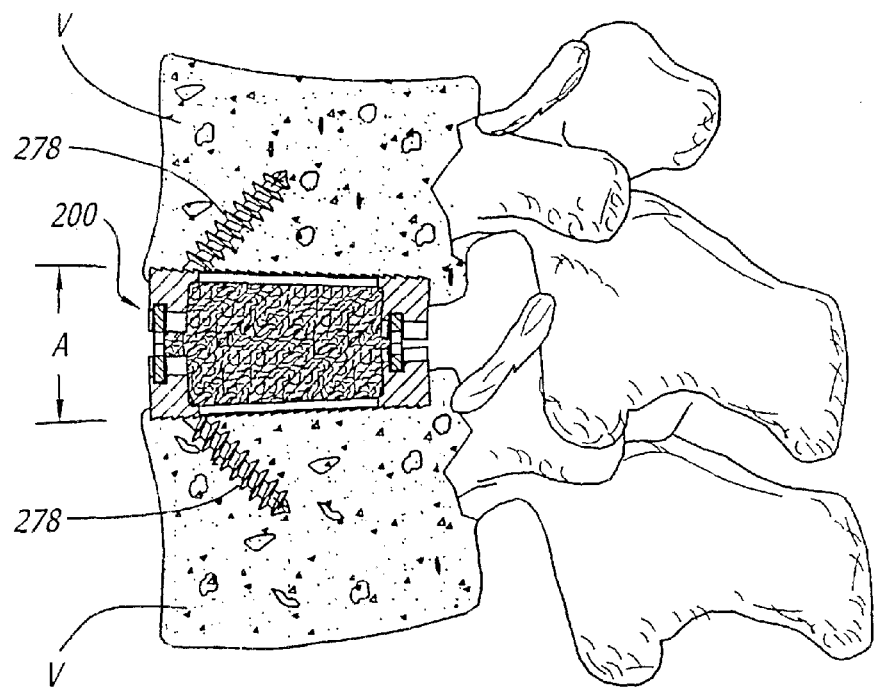
FIG. 26 is a cross-sectional side view of the implantation site formed across the space between two adjacent vertebral bodies and of the implant of FIG. 17 installed into the implantation site in the final deployed position with upper and lower surfaces in angular orientation to one another and bone screws installed to anchor the implant.
Figure 27:
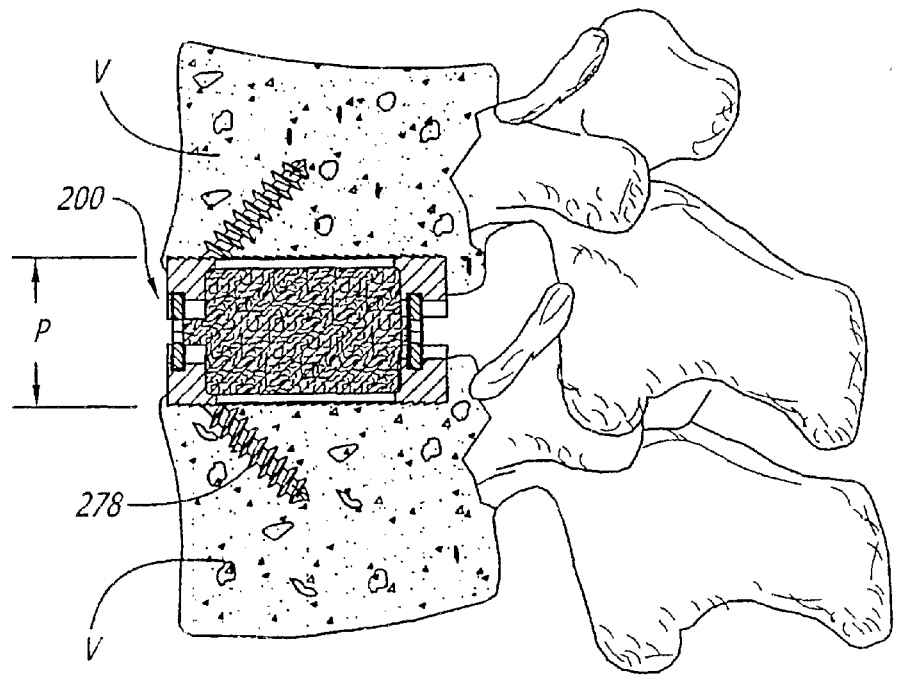
FIG. 27 is a cross-sectional side view of the implantation site formed across the space between two adjacent vertebral bodies and of the implant of FIG. 17 installed into the implantation space in the final deployed position with upper and lower surfaces in parallel orientation to one another and bone screws installed to anchor the implant.
Figure 28:
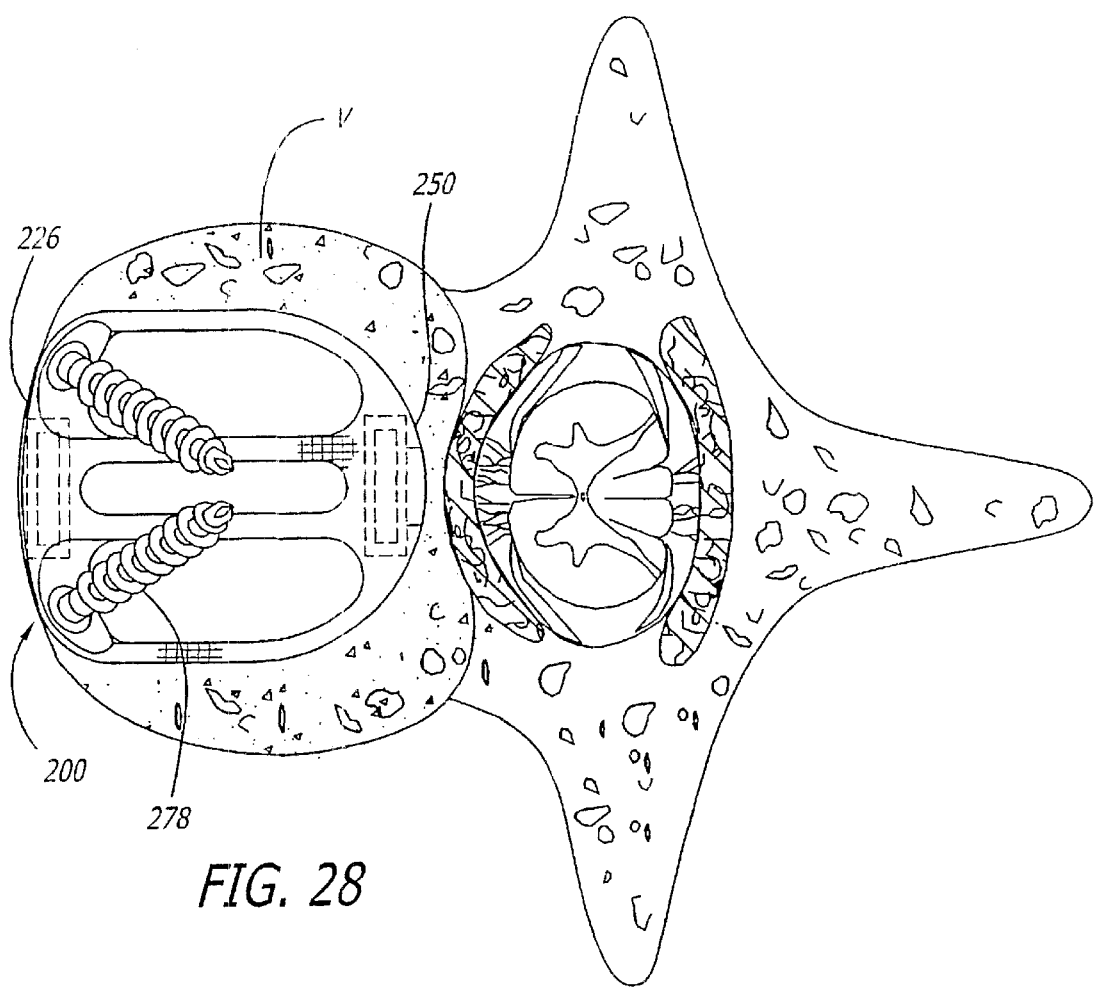
FIG. 28 is a top view the implant of FIG. 17 implanted in a final position upon the lower vertebral body of an implantation site formed anteriorly across a disc space with expander tracks shown in dashed lines and bone screws installed to anchor the implant.

In accordance with this embodiment of the present invention, a second expander 222 is located at least in part between upper and lower members 202, 206 for moving at least a portion of the upper and lower members away from one another to increase the height of implant 200 defined by the maximum distance between upper and lower surfaces 104, 108 of upper and lower members 202, 206. All of the features described herein for the single expander 122 of implant 100 of FIGS. 1–16 may also be applicable to both expanders 222 of implant 200. Additionally, second expander 222 may be located proximate an end of implant 200 opposite other expander 222, thereby providing implant 200 the capability of being expanded at both ends 226, 250 of implant 200. The increased height of implant 200 resulting from moving two expanders 222 may be the constant or varied along the length of implant 200 according to the desired configuration of implant 200. FIGS. 25 and 26 show expanders 222 moving upper and lower surfaces 204, 208 from a parallel orientation to an angled orientation relative to one another. FIGS. 25 and 27 show alternative expanders 222 moving upper and lower surfaces 204, 208 from a first height parallel orientation to a second height parallel orientation. In both events upper and lower surfaces 204, 208 in the first or insertion position are parallel to one another over a substantial portion of the length of the implant.

Figure 17:
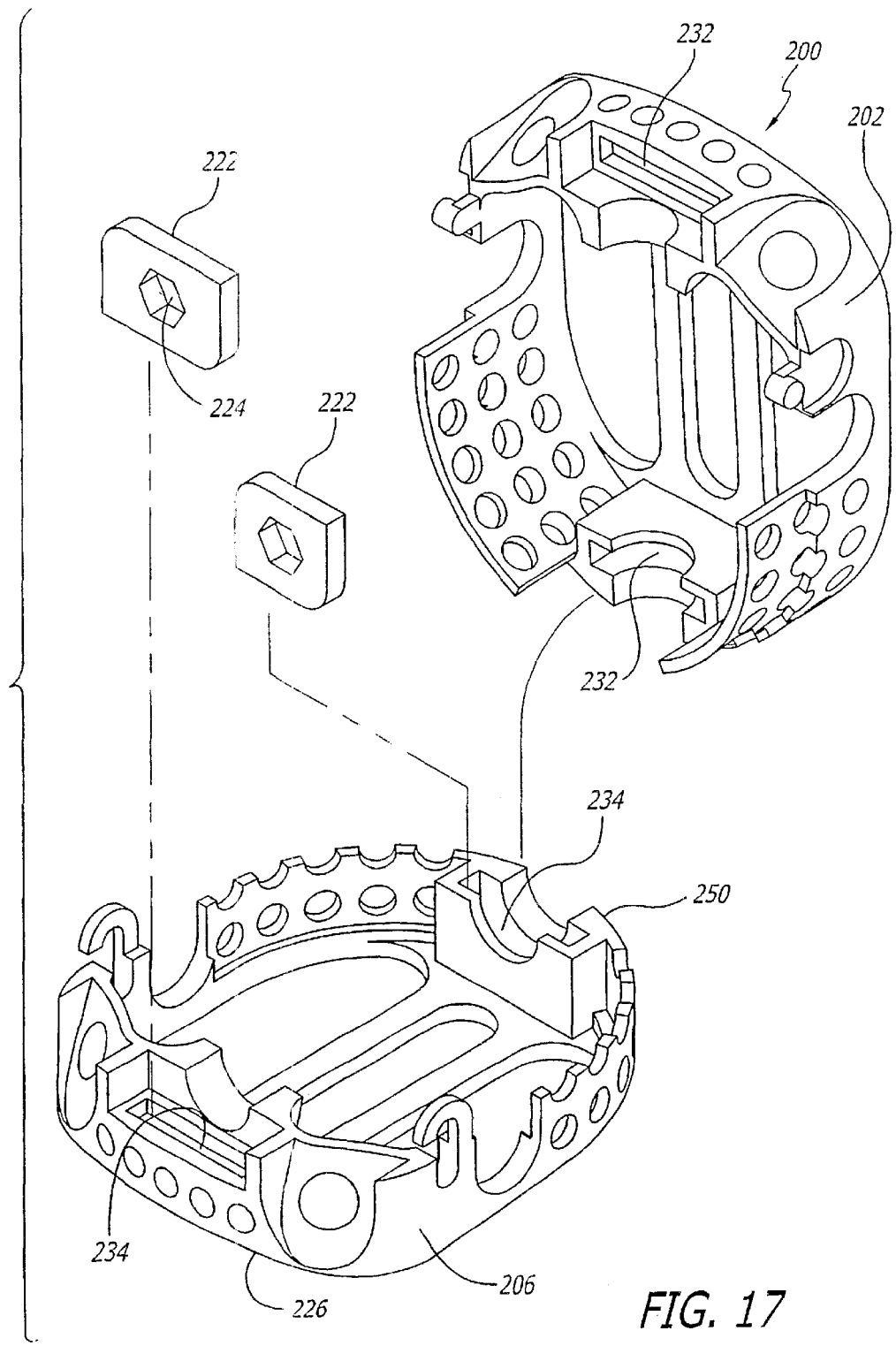
FIG. 17 is an exploded perspective view of a spinal fusion implant of another embodiment of the present invention.
Figure 20:
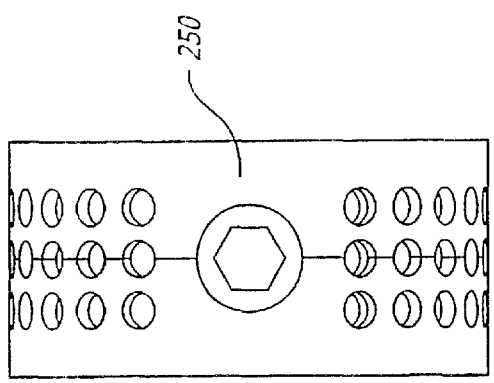
FIG. 20 is a leading end view of the implant of FIG. 17.
Figure 19:
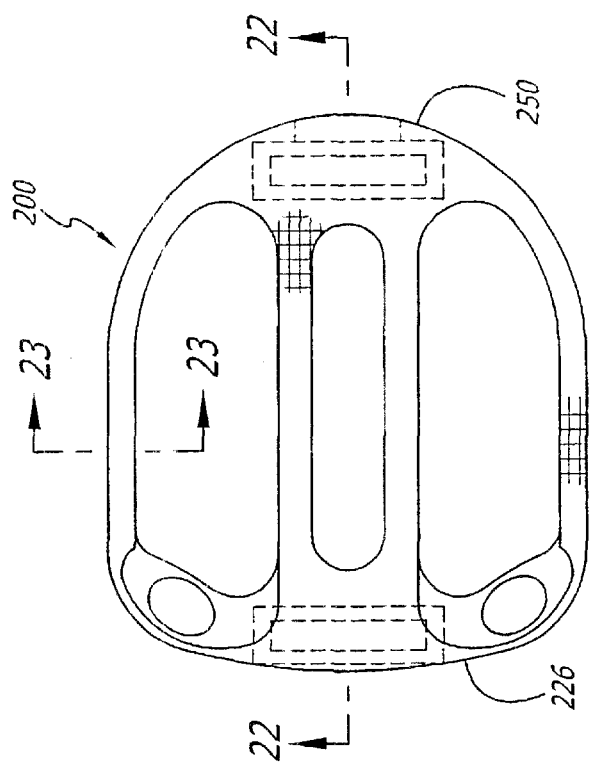
FIG. 19 is a top view of the implant of FIG. 17 with expander tracks shown in dashed lines.
Figure 18:
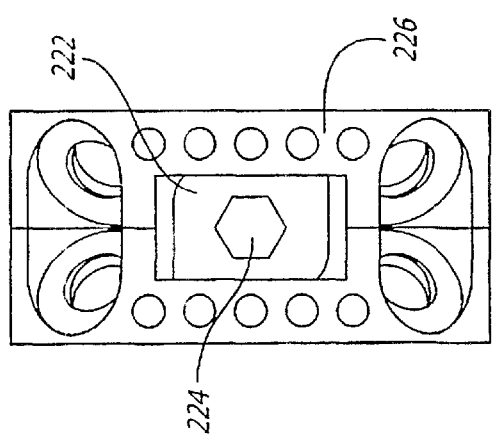
FIG. 18 is a trailing end view of the implant of FIG. 17.

As best shown in FIG. 17, tracks 232, 234 of upper and lower members 202, 206 of the second embodiment have a cooperating surface and expanders 222 have a corresponding cooperating surface that contacts the cooperating surface of tracks 232, 234 to orient expanders 222 in a predetermined location. The cooperating surfaces orient expanders 222 within implant 200 such that the axis of rotation of expanders 222 are parallel to the longitudinal axis of implant 200 and more particularly center expanders 222 within implant 200 such that the axis of rotation of expanders 222 coincide with longitudinal axis L of implant 200.

As best shown in FIGS. 25–28, another aspect of implant 200 is that its upper and lower members 202, 206 have screw holes 274 passing therethrough adapted to receive a screw 278 passing from the interior of implant 200 into adjacent vertebral bodies V to anchor implant 200 to an adjacent vertebral body V.

The articulation may be of one of two general types, examples of which are each herein disclosed. As shown in previously described embodiments of the present invention, the articulation may allow rotation about the articulation. A second type of articulation allows for both rotation and expansion at the point of articulation. An example of this is shown in FIGS. 17 and 21, where a peg and hook design is utilized. In this example both functions, that is, rotation or pivoting, and captured or limited expansion with a fixed end point or stop, occur at the same location. Alternatively, and without departing from the teachings of the present invention, those functions can be divided. By way of example only, and not limitation, expansion can be allowed and controlled by an interlocking wall design, as shown by the interlocking members in the alternative embodiments of FIGS. 23A and 23B. FIG. 23A is a partial cross sectional view of an embodiment of an interlocking wall design shown in the collapsed state for implants of the present invention. FIG. 23B is a partial cross sectional view of an embodiment of the interlocking wall design of FIG. 23A shown in a partially expanded position for implants of the present invention. Various other structural features as would be obvious to one of ordinary skill in the art after the teachings herein can similarly be employed.

A fixed end point for the implant expansion is preferred for the proper functioning of the opposed bone screws. A purpose of the opposed bone screws is to rigidly secure the implant within the vertebral segment. A further purpose is to pull each of the adjacent vertebral bodies toward the implant and towards each other so as to have a construct resistant to the deleterious effects of vertebral rocking as may otherwise occur with spinal flexion and extension absent such restraint. If the articulation device captures the upper and lower members together, as in the embodiment of posterior implant 100 of FIGS. 1–16, by closely encircling a post then the implant cannot expand at that location. So the coupling mechanism of FIGS. 17 and 21 permit the upper and lower members to remain articulated, permit the implant to expand, and permit the screws to pull against the implant and each other, in opposite directions and to pull the bones toward each other. An optional extended slot and peg configuration may be added toward leading end 250 of implant 200, however, this is not needed to hold the implant together.

Figure 29:
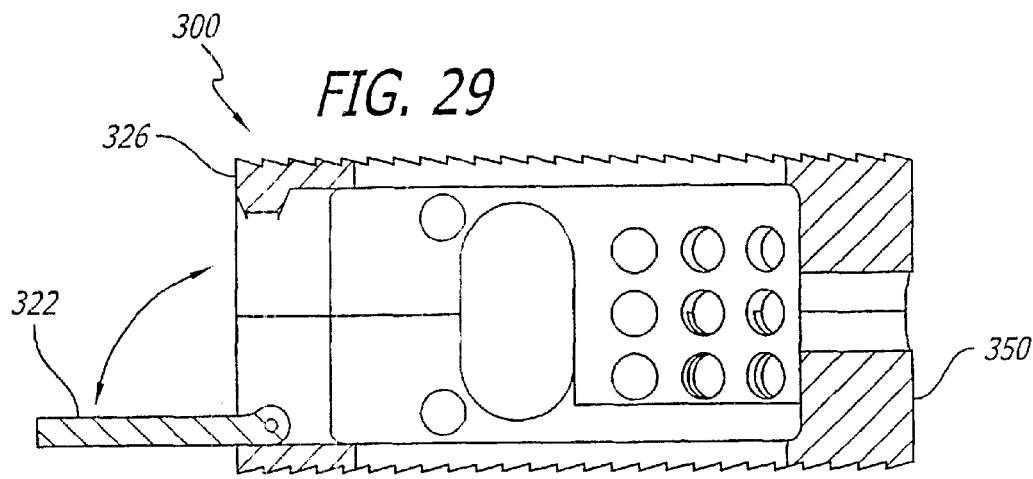
FIG. 29 is a cross-sectional side view of an alternative embodiment of an implant of the present invention with a pivoting trailing end that is also a blocker with the trailing end in the open position.
Figure 30:
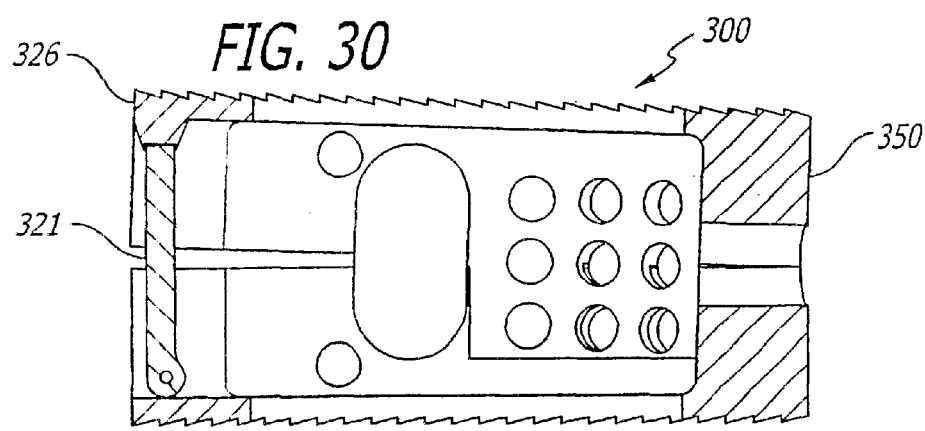
FIG. 30 is a cross-sectional side view of an alternative embodiment of an implant of FIG. 29 with the trailing end in the closed position.
Figure 31:
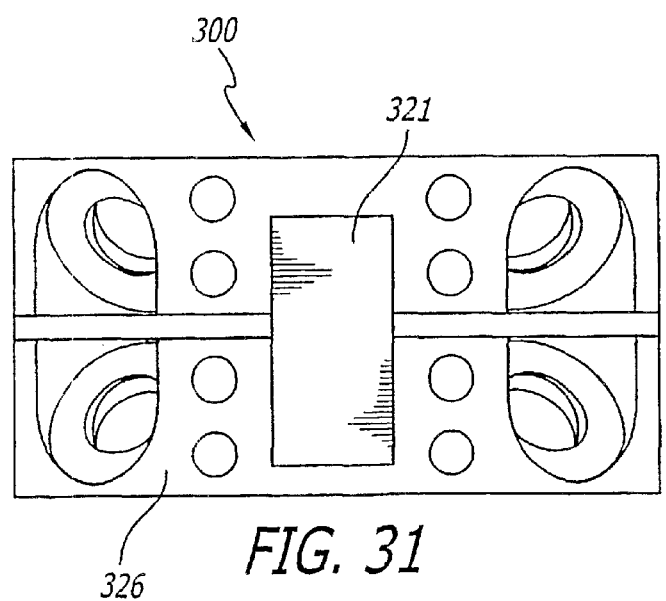
FIG. 31 is a trailing end perspective view of the implant of FIG. 30

An alternative embodiment of an implant for use from the anterior approach is shown in FIGS. 29 through 31. In implant 300 blocker 322 takes the form of a trailing wall that articulates or hinges to the inside of implant 300. The trailing wall may be left open during insertion of implant 300 so as to trail behind the upper and lower members. Once implant 300 is implanted into position, the trailing wall is rotated about one of its ends and pushed into position and locked into place. This may occur by having the trailing wall contact an inclined plane that leads up to a notch into which the trailing wall locks into place. The trailing wall itself may also have at least one opening in it to permit the further loading of fusion-promoting materials into implant 300. Blocker 322 may also be adapted to cooperatively engage a tool used to move the blocker from an initial position to a final position to increase the height of implant 300, the tool being removable after moving blocker 322 into the final position.

Implant 300 may be configured to have a rotational articulation between the upper and lower members adjacent one of the ends of the upper and lower members. The rotational articulation may be formed by the upper and lower members interdigitating so as to cooperatively engage. The rotational articulation may be configured so that engagement occurs when the upper and lower members are substantially perpendicular to one another. The rotational articulation may also be configured to remain engaged within a range of movement of the upper and lower members resulting from positioning implant 300 between a first position of the upper and lower members relative to one another allowing for a collapsed implant height and a second position relative to one another allowing for an increased implant height.

At least one or both of the upper and lower members of implant 300 may be configured to have a screw hole passing therethrough that is adapted to receive a screw passing from an interior of implant 300 into an adjacent vertebral body. The screw may be adapted to pass from the interior of implant 300 through the screw hole and into the adjacent vertebral body to anchor implant 300 to the adjacent vertebral body.

Implant 300 may be configured to have a side surface contoured to cooperate with another implant when implant 300 is in a final position. Implant 300 and the cooperating implant may have a combined width therebetween less than the combined height of implant 300 and the cooperating implant.

Figure 32:
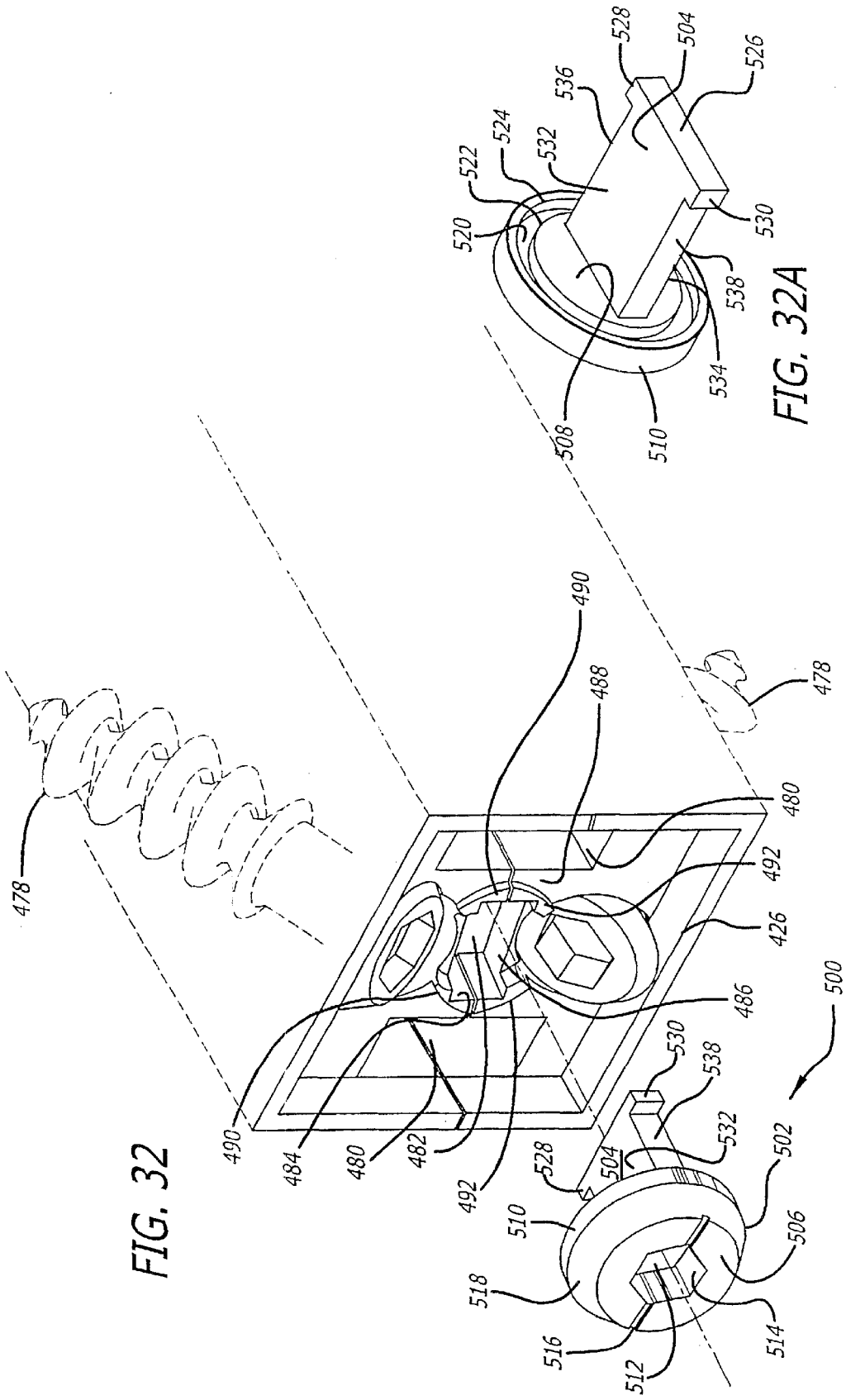
FIG. 32 is a partial fragmentary exploded front perspective view of an expandable interbody spinal fusion implant with expanding and locking end cap in accordance with a preferred embodiment of the present invention.
Figure 33:
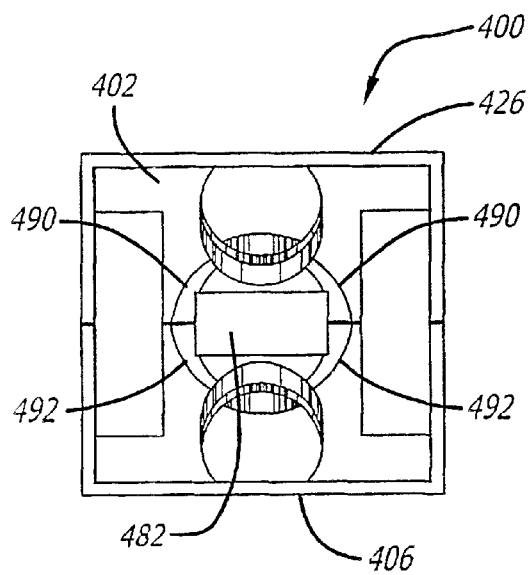
FIG. 33 is a rear elevation view of the implant of FIG. 32.

FIGS. 32–37 show a preferred embodiment of an expandable interbody spinal fusion implant 400 and an expanding and locking end cap 500 for use therewith in accordance with the present invention. As shown in FIGS. 32 and 33, implant 400 preferably has a trailing end 426 that includes openings 480 to permit for the growth of bone through implant 400. Implant 400 has a bone-engaging projection that is preferably one of ratchets, splines, knurling, or other surfaces rougheners to resist expulsion of the implant from the disc space after implantation.

Figure 35:
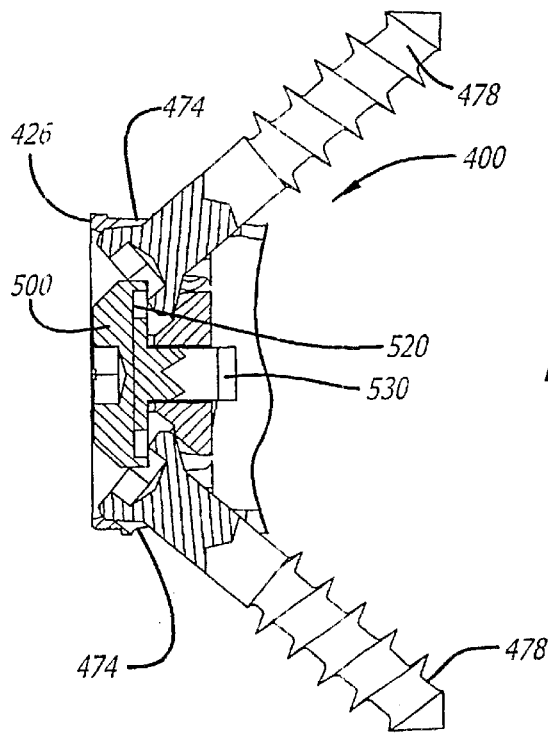
FIG. 35 is a side elevation view in partial cross section of the implant of FIG. 32 in an unexpanded state and end cap inserted therein.
Figure 36:
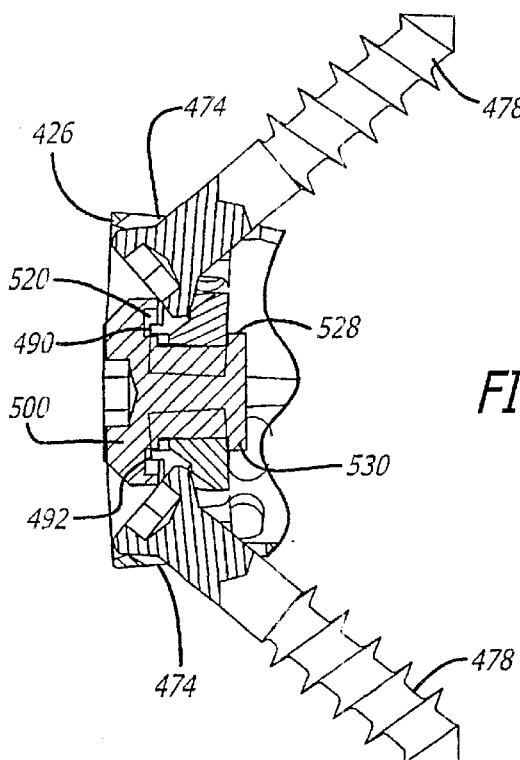
FIG. 36 is a side elevation view in partial cross section of the implant of FIG. 32 in an expanded state and end cap inserted therein.
Figure 38:
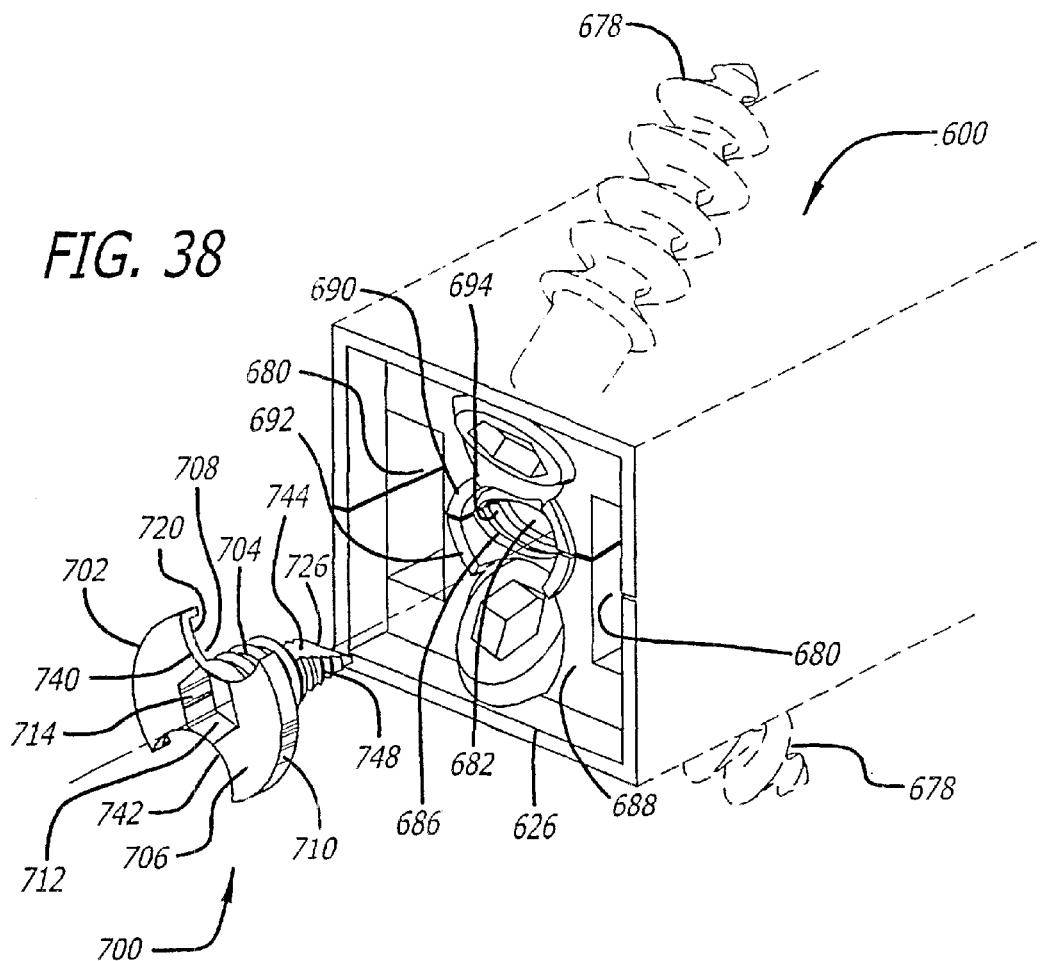
FIG. 38 is a front perspective view of an expandable interbody spinal fusion implant with expanding and locking end cap in accordance with another preferred embodiment of the present invention.
Figure 39:
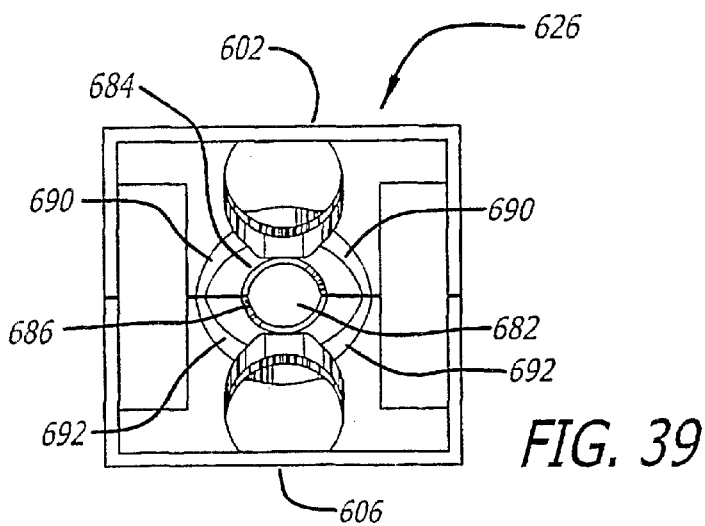
FIG. 39 is a rear elevation view of the implant of FIG. 38.

As shown in FIGS. 35 and 36, by way of example, upper and lower members 402, 406 preferably have upper and lower screw holes 474 passing therethrough, each adapted to receive a bone screw 478 passing from the interior of implant 400 into an adjacent vertebral body to anchor implant 400 to an adjacent vertebral body. Bone screws are not essential to the operation of the invention, but are preferable for providing added securement of the implant to the adjacent vertebral bodies.

In certain circumstances, upper and lower members 402, 406 can move away from one another and merely securing upper and lower members 402, 406 to the adjacent vertebral bodies with bone screws is not adequate. An example of such a circumstance occurs when the surgeon elects to approach the spine anteriorly, which generally requires severing and/or removing substantial portions of the anterior longitudinal ligament over the operated area. The anterior longitudinal ligament is positioned along the anterior spinal surface and prevents hyperextension of the spine as an individual bends backward. Because the anterior longitudinal ligament covers the anterior spinal surface, the surgeon must cut through this tough ligament to access the disc space below, compromising the stability of the spine. Specifically, the anterior longitudinal ligament is generally lax, except when an individual leans backward, then the ligament acts as a tension band resisting elongation. If the anterior longitudinal ligament is damaged, there is no check on that spinal movement and the vertebral bodies may detrimentally angulate. Thus, a mechanism is needed to prevent movement of the upper and lower members relative to one another beyond a predetermined amount.

FIGS. 32–33 show expanding and locking end cap 500 for use with implant 400. The end cap is capable of one or more of the following functions: (1) expands the implant by moving the upper and lower members apart, (2) maintains the implant in an expanded state by holding at least a portion of the upper and lower members apart so as to maintain the increased height of the implant and resist the collapse of the implant to the collapsed implant height, (3) prevents the implant from expanding beyond a predetermined amount by engaging at least a portion of the upper and lower members, and (4) locks bone screws to the implant by blocking the exit path of the bone screws in a direction opposite to the direction of insertion. Expansion of the implant preferably increases the implant height only, that is in a plane passing through the mid-longitudinal axis of the implant and the upper and lower members. In a preferred embodiment, the end cap is capable of performing all four of the aforementioned functions.

As shown in FIGS. 32 and 33, trailing end 426 of implant 400 preferably has an opening 482 adapted to engage cap 500 and may also provide access to the interior of implant 400 for the purpose of introducing bone growth promoting materials therein. Upper and lower interior surfaces 484, 486 of opening 482 preferably have a portion that extends beyond exterior trailing end surface 488, forming upper lip portions 490 and lower lip portions 492, respectively. When implant 400 is in an unexpanded state, the profile of upper and lower lip portions 490, 492 preferably form the shape of at least a portion of an oval. In the expanded state of implant 400, the profile of upper and lower lip portions 490, 492 preferably becomes less oval and generally more circular in shape. For example, upper and lower lip portions 490, 492 can be arcs of a circle such that in the expanded state, the arcs would be part of the same circle.

Cap 500 has a head 502 and a stem 504. Head 502 has a perimeter preferably sized and shaped to cover at least a portion of upper and lower bone screw holes 474 so as to lock bone screws 478 to implant 400. Head 502 has a top surface 506, a bottom surface 508, and a rim 510. Top surface 506 has a tool engagement area 512 that is preferably adapted to cooperatively engage an insertion tool. Tool engagement area 512 preferably includes a hex-shaped recess 514 and a groove 516 adapted to engage correspondingly-shaped tools, respectively. Other shapes are possible for tool engagement area 512 depending upon the type of insertion tool used with the present invention, all of which are within the broad scope of the present invention.

Top surface 506 of cap 500 preferably has a bevel 518 extending around the perimeter thereof to form a reduced profile. Top surface 506 may have any shape suitable for its intended purpose and it is preferable that such shape does not extend from trailing end 426 so as not to substantially interfere with delicate vascular and neurological structures adjacent thereto after implant 400 is installed in the spine.

As shown in FIG. 32A, bottom surface 508 of cap 500 has a recess 520 proximate the perimeter of bottom surface 508 that is adapted to interact with upper and lower lip portions 490, 492 of implant 400. As described in further detail below, the interaction of lip portions 490, 492 and recess 520 limits the over-expansion of implant 400. Recess 520 has an inner perimeter 522, an outer perimeter 524, and a width therebetween adapted to accommodate the profiles of at least a portion of upper and lower lips 490, 492 of implant 400 in both an unexpanded and expanded state. The surface of outer perimeter 524 forms a flange that acts as a stop against which upper and lower lip portions 490, 492 of implant 400 are prevented from further movement away from the mid-longitudinal axis of implant 400 when implant 400 and cap 500 are engaged, as will be described in more detail below.

Stem 504 of cap 500 projects from bottom surface 508 and is sized and shaped to cooperatively engage opening 482 in trailing end 426 to expand implant 400 and to maintain implant 400 in an expanded state. Stem 504 preferably has a distal end 526 with tabs 528, 530, an upper surface 532, a lower surface 534 opposite to upper surface 532, and sides 536, 538. Tabs 528, 530 are configured to engage the interior surface of trailing end 126 such that when properly positioned within opening 482, tabs 528, 530 prevent cap 500 from backing out of opening 482 of implant 400.

Sides 536, 538 of stem 504 are configured to cooperatively engage upper and lower interior surfaces 484, 486 of opening 482. Opening 482 may have any shape suitable for its intended purpose for interacting with stem 504. For example, sides 536, 538 may be beveled or rounded to accommodate rotational contact with upper and lower interior surfaces 484, 486. Stem 504 may have a generally rectangular cross-section or may have a cross-section with sides 536, 538 intersecting the upper and the lower surfaces 532, 534 at junctions, which may be two diametrically opposed corners and two diametrically opposed arcs. The two diametrically opposed arcs may be each of the same radius and, preferably, the diagonal or modified hypotenuse "MH" between the opposed arcs has a maximum dimension that generally approximates the distance between the upper and lower surfaces 532, 534 such that, when stem 504 is rotated from a first insertion position toward a second/deployed position, no substantial over-distraction occurs between the adjacent vertebral bodies as would occur if the height of the implant was increased markedly beyond that obtained in the second/deployed position. The two diametrically opposed corners may form a 90-degree angle. Additionally, sides 536, 538 may be configured to be divergent away from distal end 526 to better accommodate engagement with upper and lower interior surfaces 484, 486 while implant 400 is in the expanded state.

Figure 34:
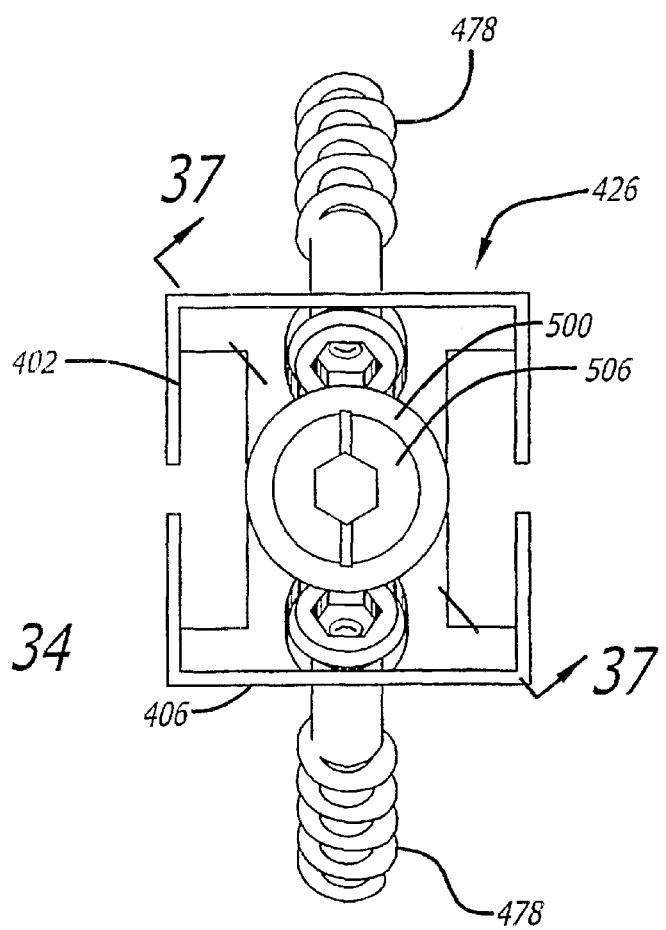
FIG. 34 is a rear elevation view of the implant of FIG. 32 in an expanded state and end cap inserted therein.

FIGS. 34–36 show a preferred expansion of implant 400 by cap 500. In FIG. 35, stem 504 of cap 500 is inserted through opening 482 in trailing end 426 of implant 400. After stem 504 is inserted into opening 482, tabs 528, 530 extend beyond upper and lower interior surfaces 484, 486 of opening 482 and into the interior of implant 400. Upper and lower surfaces 532, 534 of stem 504 are oriented toward upper and lower interior surfaces 484, 486 of opening 482, respectively, such that implant 400 is in a collapsed state. As cap 500 is rotated 90° in either direction, sides 536, 538 of stem 504 cooperatively engage with upper and lower interior surfaces 484, 486 of opening 482, forcing apart upper and lower members 402, 406 away from the mid-longitudinal axis of implant 400 to position implant 400 in an expanded state. The rotation of cap 500 moves upper and lower members 402, 406 from a generally parallel orientation shown in FIG. 35 to an angled orientation shown in FIG. 36. During expansion of implant 400, upper and lower lip portions 490, 492 move within recess 520 of cap 500 until stem 504 ceases moving upper and lower interior surfaces 484, 486 away from the mid-longitudinal axis of implant 400.

Figure 37:
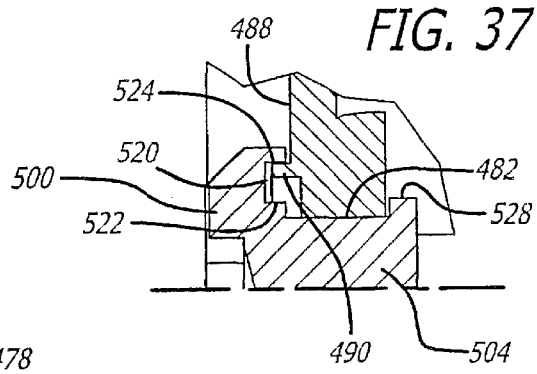
FIG. 37 is a fragmentary cross sectional side elevation view of the implant of FIG. 32 in an expanded state showing a lip portion of the implant trailing end against the outer perimeter of a recess in the end cap for preventing over-expansion of the implant.

FIG. 37 shows a partial cross-section along line 37—37 of FIG. 34. As shown in FIG. 37, the maximum expansion of upper member 402 is reached when upper lip portions 490 are blocked from further motion away from the mid-longitudinal axis of implant 400 upon reaching outer perimeter 524 of recess 520. Although not shown in FIG. 37, lower lip portions 492 similarly contact outer perimeter 524 of recess 520. In this manner, the expansion of implant 400 beyond a predetermined amount is prevented. Tabs 528, 530 of stem 504 bear against the interior of implant 400 and prevent removal of end cap 500 from opening 482. In the deployed position, end cap 500 locks implant 400 in an expanded state.

As shown in FIGS. 38–41, another preferred embodiment of the implant and end cap of the present invention is shown and generally referred to by the reference numbers 600 and 700, respectively. Implant 600 is similar to implant 400, except that opening 682 of implant trailing end 626 preferably has at least one thread 694 for cooperatively engaging with a threaded stem 404 of cap 700.

Cap 700 is similar to cap 500, except for differences noted below. Head 702 includes an upper cutout portion 740 and a lower cutout portion 742, each being adapted to allow the passage of a bone screw 678 into implant 600 after cap 700 has been attached to implant 600. Once bone screws 678 are inserted, cap 500 may be rotated such that at least a portion of head 702 covers each of screws 678. Upper and lower cutout portions 740, 742 allow the surgeon the option of inserting bone screws 678 before or after attachment of cap 700 with implant 600.

Stem 704 has at least one thread 748 along the mid-longitudinal axis of cap 700 for cooperatively engaging with threaded opening 682 of implant 600. Distal end 726 of stem 704 has an upper surface 744 and a lower surface 746 that are convergent towards distal end 726 for assisting in the insertion of stem 704 into opening 682 of implant 600.

Figure 40:
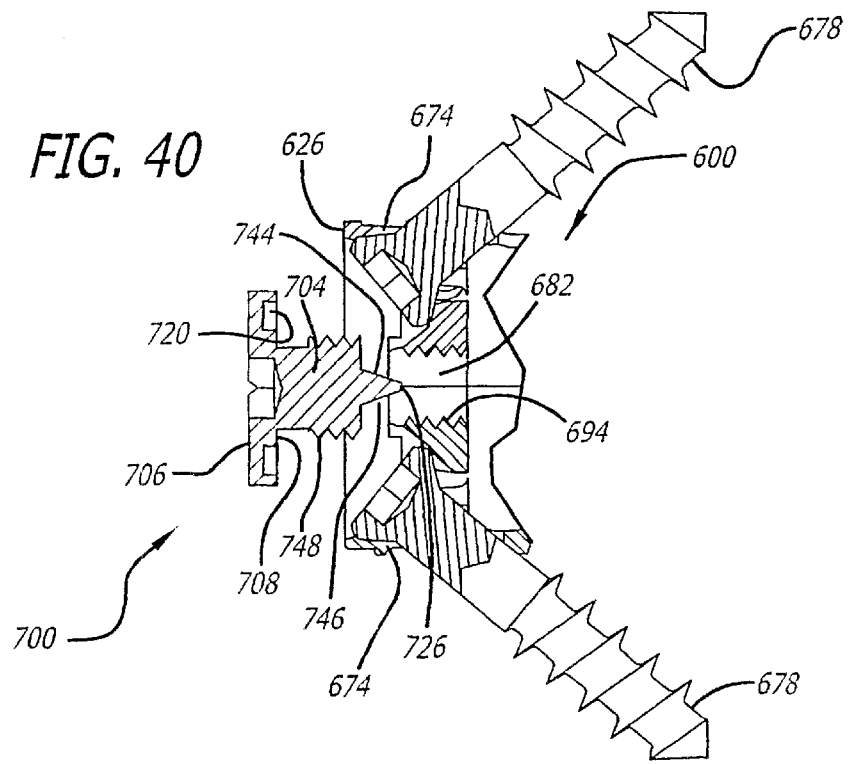
FIG. 40 is a side elevation view in partial cross section of the implant of FIG. 38 in an unexpanded state and end cap being inserted therein.
Figure 41:
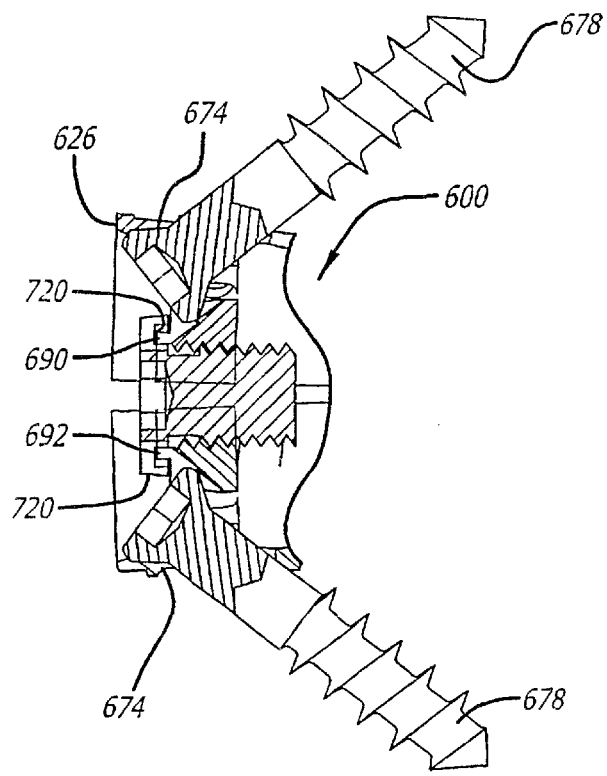
FIG. 41 is a side elevation view in partial cross section of the implant of FIG. 38 in an expanded state and end cap inserted therein.
Figure 44:
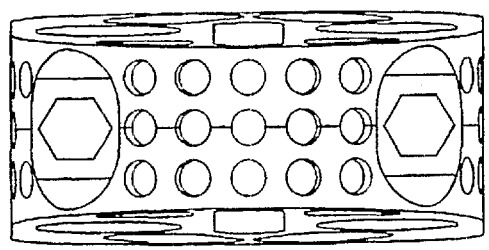
FIG. 44 is a leading end view of the implant of FIG. 42.
Figure 43:
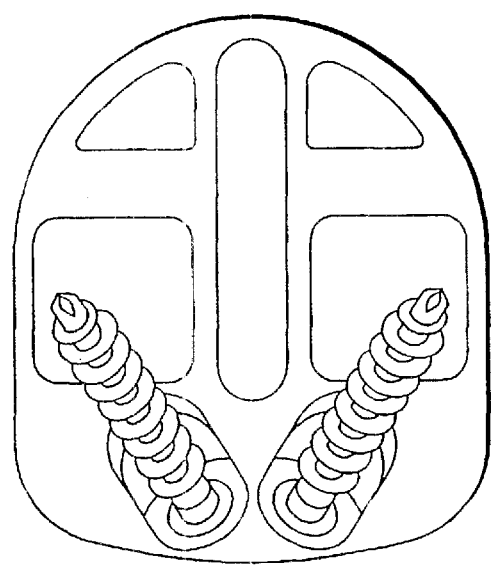
FIG. 43 is a top plan view of the implant of FIG. 42 with bone screws installed.
Figure 45:
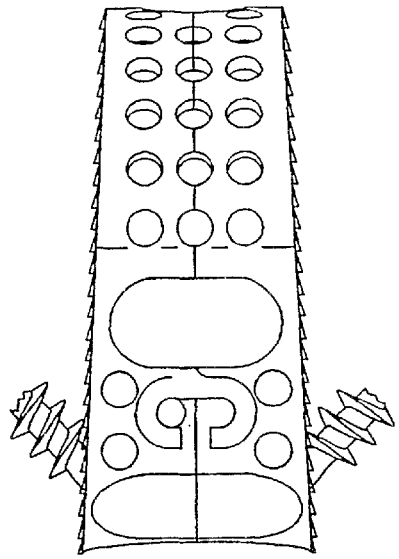
FIG. 45 is a side elevation view of the implant of FIG. 43.
Figure 42:
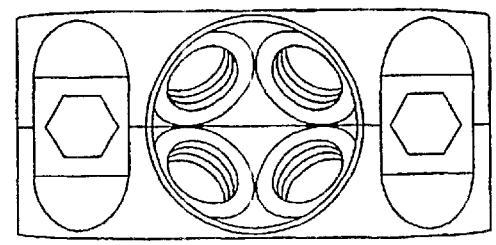
FIG. 42 is a trailing end view of another preferred embodiment of the implant of the present invention having four expanders and adapted to be inserted from an anterior approach to the spine.
Figures 50, 51, 52, 53, 54:
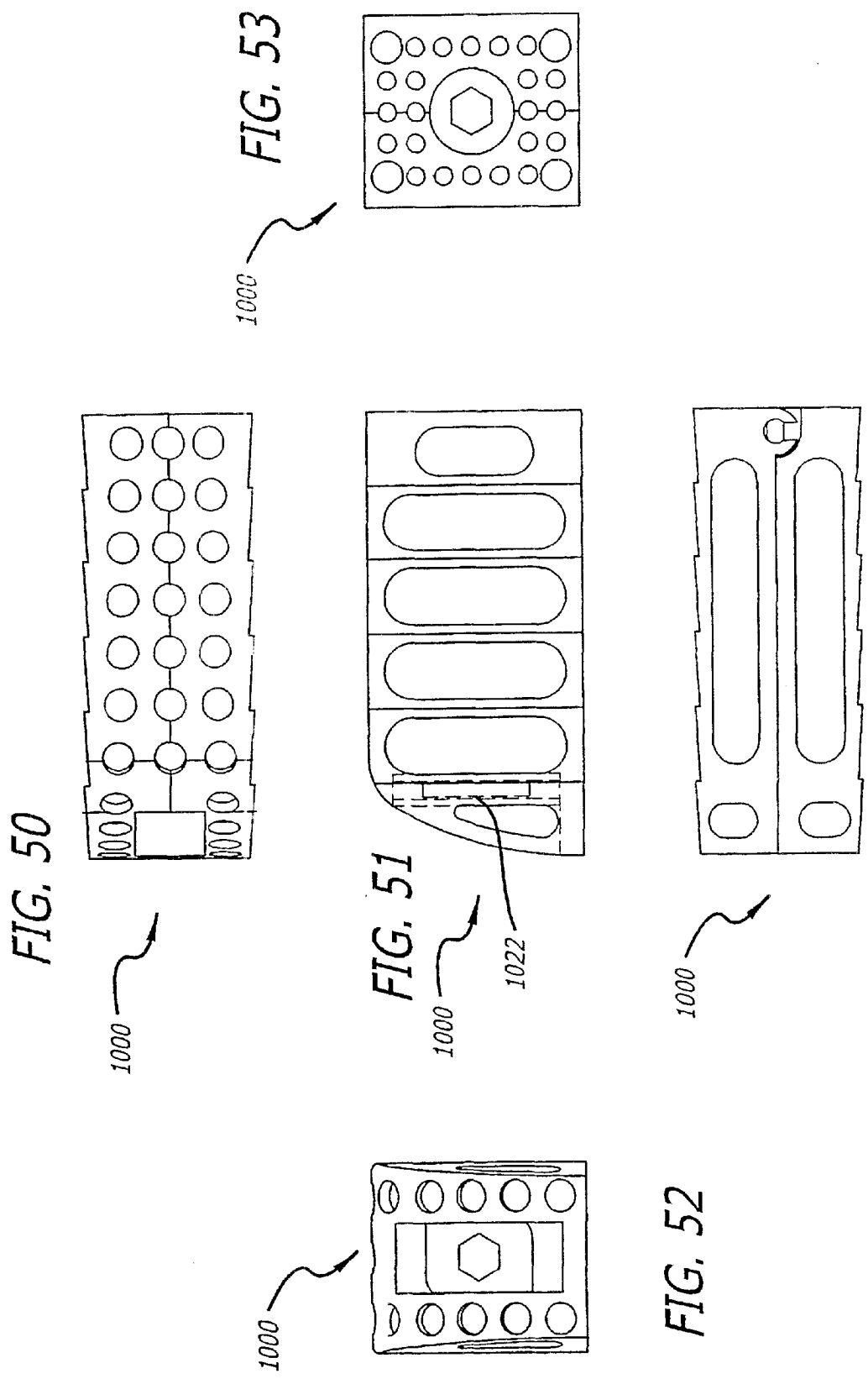
FIG. 50 is an exterior facing side elevation view of another preferred embodiment of an implant of the present invention adapted to be inserted from a posterior approach to the spine preferably in pairs.
FIG. 51 is a top plan view of the implant of FIG. 50.
FIG. 52 is a leading end view of the implant of FIG. 50.
FIG. 53 is a trailing end view of the implant of FIG. 50.
FIG. 54 is an interior facing side elevation view of the implant of FIG. 50.

As shown in FIGS. 40 and 41, cap 700 is inserted into trailing end 626 of implant 600, preferably by aligning the edge of distal end 726 with the plane separating upper and lower members 602, 606. Once upper and lower surfaces 744, 746 of distal end 726 are sufficiently within threaded opening 682 of implant trailing end 626, cap 700 is rotated to allow stem thread 748 of cap 700 to cooperatively engage with threaded opening 682. The engagement of stem thread 748 with threaded opening 682 spreads apart upper and lower members 602, 606 at least along a portion of the length of implant 600. Continued rotation of cap 700 forces upper and lower lip portions 690, 692 to contact recess 720 of cap 700. The pitch of thread 748 is preferably such that as upper and lower lip portions 690, 692 reach recess 720, they come into contact with at least a portion of the outer perimeter of recess 720. Upon contact with recess 720, upper and lower lip portions 690, 692 are prevented from further movement away from the mid-longitudinal axis of implant 600.

Those skilled in the art will appreciate that although it is preferred to use a cap to prevent over-expansion of an expandable implant, the invention is not so limited. For example, the implant trailing end may be adapted to have lip portions along the trailing end interior surface for cooperatively engaging with a recess and/or flange to prevent over-expansion of the implant. In such an instance, an over-expansion inhibiting surface may operate without a stem and/or head by relying on additional surface features of the implant trailing end, for example, a key-way entry along the opening leading to the interior lip portions or a circumferential barrier beyond the interior lip portions for preventing the over-expansion surface from traveling too far into the implant interior. Although the expander implant cap has been described with respect to a threaded expanding spinal fusion implant, it may be adapted for use with any expandable spinal implants including any of the various implant embodiments disclosed herein.

FIGS. 42–46 show another preferred embodiment of the implant 800 that is adapted to be inserted from an anterior approach to the spine. In implant 800 two sets of expanders 822 are used, each set being located on one side of the mid-longitudinal axis of implant 800. Depending upon the type of articulation used, expanders 822 may be rotated to confer a transverse angulation as well as longitudinal angulation to the upper and lower members of implant 800 in situations where such angulation is desired. All four expanders 822 may be used to expand the upper and lower members of implant 800 by the same or different amount relative to one another. This can be done to permit the surgeon to expand the leading and trailing ends or sides by varying degrees.

Another aspect of implant 800 is that its upper and lower members have screw holes passing therethrough adapted to receive a bone screw passing from the interior of implant 800 into adjacent vertebral bodies to anchor implant 800 to an adjacent vertebral body. A purpose of the opposed bone screws is to rigidly secure the implant within the vertebral segment. A further purpose is to pull each of the adjacent vertebral bodies toward the implant and towards each other.

FIG. 47 shows a preferred embodiment of an end cap 898 for locking the bone screws to implant 800. The end cap is preferably configured to threadably engage the opening in the trailing end of implant 800.

FIGS. 48 and 49 show a preferred embodiment of a bone screw 900 for use with implant 800. Bone screw 900 preferably has a threaded head portion to threadably engage the screw holes of implant 800. Bone screw 900 is self-locking since the thread pattern of the head is different from the thread pattern along the shaft of the screw that penetrates the bone. It is appreciated that bone screws are not essential to the operation of the invention, but are preferable for providing added securement of the implant to the adjacent vertebral bodies.

FIGS. 50–54 show another preferred embodiment of an implant 1000 of the present invention adapted to be inserted from a posterior approach to the spine. Implant 1000 is preferably installed in pairs, to either side of the mid-sagittal axis of the vertebral bodies. Each implant 1000 in the pair is preferably a mirror image of the other. Implant 1000 preferably has a leading end for placement toward the anterior aspect of the vertebral bodies that is configured to conform to at least a portion of the anterior aspect of the vertebral bodies. The upper and lower members are preferably articulated at the trailing end of implant 1000. An expander 1022 located proximate the leading end of implant 1000 is used to angulate the upper and lower members of implant 1000 to place the adjacent vertebral bodies in proper lordosis. Expander 1022 is manipulated by a tool inserted from a posterior approach through the trailing end of the implant. For insertion from an anterior approach to the spine, it is appreciated that in an alternative embodiment, expander 1022 may be located proximate the trailing end of the implant with the upper and lower members being articulated at the leading end of the implant.

The expandable push-in spinal fusion implant may include, be made of, treated, coated, filled, in combination with, or have a hollow for containing artificial or naturally occurring materials suitable for implantation in the human spine. These materials include any source of osteogenesis, bone growth promoting materials, bone derived substances, bone morphogenetic proteins, hydroxyapatite, genes coding for the production of bone, and bone including, but not limited to, cortical bone. The implant can also be formed of material such as metal including, but not limited to, titanium and its alloys or ASTM material, surgical grade plastics, plastic composites, ceramics, or other materials suitable for use as a push-in spinal fusion implant.

The implant can include in part of materials that are bioabsorbable in the body. The push-in implant of the present invention can be formed of a porous material.

The present invention is directed to expandable push-in implants only not including push-in implants having substantially arcuate upper and lower members oriented toward the adjacent vertebral bodies and designed to engage the vertebral bodies only along arcuate cuts therein typically formed by a drill. Further, the present invention is not directed to threaded implants requiring rotation for insertion into the implantation space in the spine. The implant of the present invention does not have a circular cross-section along a substantial portion of its length.

While various embodiments of the present invention are presented by way of example only and not limitation, common to each of them, is that the expandable push-in spinal fusion implant adapted for linear insertion across disc space D between two adjacent vertebral bodies V of a human spine has an upper member having an upper surface adapted for placement toward and in contact with the upper of the adjacent vertebral bodies V. The implant also has a lower member having a lower surface adapted for placement toward and in contact with the lower of the adjacent vertebral bodies V. The upper and lower surfaces of the upper and lower members have at least one opening. The openings of the upper and lower surfaces are in communication with one another to permit for the growth of bone from vertebral body V to adjacent vertebral body V through the implant. Preferably, on the exterior of each of the opposed upper and lower surfaces of the upper and lower members is at least a portion of a bone-engaging projection adapted for linear insertion. A blocker in the form of an expander preferably is located proximate at least one of the ends to hold at least a portion of the upper and lower members apart from one another to increase the implant height.

There is disclosed in the above description and the drawings implants, which fully and effectively accomplish the objectives of this invention. However, it will be apparent that variations and modifications of the disclosed embodiments may be made without departing from the principles of the invention or the scope of the appended claims.

What is claimed is:

1. A push-in interbody spinal fusion implant for linear insertion at least in part across at least the height of a disc space between two adjacent vertebral bodies of a spine, said implant comprising:

an upper member having an upper surface adapted for placement toward and into contact with one of the adjacent vertebral bodies from within the disc space, said upper surface being non-arcuate along a substantial portion of the length of said implant, said upper surface having at least one opening therethrough and adapted to contact one of the adjacent vertebral bodies, said upper member having a proximal end and a distal end;

a lower member having a lower surface adapted for placement toward and into contact with the other of the adjacent vertebral bodies from within the disc space, said lower surface being non-arcuate along a substantial portion of the length of said implant, said lower surface having at least one opening therethrough and adapted to contact the other of the adjacent vertebral bodies, said openings of said upper and lower surfaces being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height of at least a portion of said implant; and a blocker pivotally attached to one of said upper and lower members proximate one of said proximal and distal ends and being adapted to pivot into cooperative engagement with another of said one of said upper and lower members, said blocker being adapted to hold at least a portion of said upper and lower members apart so as to maintain the increased height of said implant and resist the collapse of said implant to the collapsed implant height when said implant is in a final deployed position, said implant having a width and said blocker having a width less than the width of said implant.

2. The push-in implant of claim 1, further comprising a hollow defined between said upper and lower members in communication with said openings in each of said upper and lower surfaces, said hollow being adapted to receive fusion-promoting substances.

3. The push-in implant of claim 2, wherein said hollow has a width that is unobstructed by any mechanism for moving said blocker.

4. The push-in implant of claim 2, wherein said implant has a constant width in both the collapsed height and the increased height.

5. The push-in implant of claim 2, wherein said blocker is located at least in part between said upper and lower members.

6. The push-in implant of claim 2, wherein said blocker is pivotally attached to said proximate end, said blocker being configured to rotate towards said distal end.

7. The push-in implant of claim 2, wherein said blocker is a portion of one of said ends of said upper and lower members.

8. The push-in implant of claim 2, wherein said blocker is adapted to cooperatively engage a tool used to move said blocker from an initial position to a final position to increase the height of said implant, said tool not being a part of said implant and being removed from said implant after moving said blocker into the final position.

9. The push-in implant of claim 2, wherein said blocker has a width less than one half the width of said implant.

10. The push-in implant of claim 2, wherein said implant has side walls and said blocker does not contact said side walls when said implant is in the final deployed position.

11. The push-in implant of claim 2, wherein said blocker moves said upper and lower surfaces of said upper and lower members from a parallel orientation to an angled orientation relative to one another.

12. The push-in implant of claim 2, wherein at least one of said upper and lower members is configured to cooperate with a projection so as to stop said upper and lower members from being moved apart from one another more than a predetermined distance.

13. The push-in implant of claim 2, wherein said upper and lower members are configured to cooperate with one another so as to stop said upper and lower members from being moved apart from one another more than a predetermined distance.

14. The push-in implant of claim 2, wherein said upper and lower members have walls contacting one another.

15. The push-in implant of claim 14, wherein said walls are aligned parallel with the longitudinal axis of said implant.

16. The push-in implant of claim 14, wherein said walls are at least in part overlapping.

17. The push-in implant of claim 2, wherein said upper and lower members have a rotational articulation therebetween adjacent one of said proximal end and said distal end of said upper and lower members.

18. The push-in implant of claim 17, wherein said rotational articulation is at one of said proximal end and said distal end of said upper and lower members opposite said blocker.

19. The push-in implant of claim 17, wherein said rotational articulation allows for expansion.

20. The push-in implant of claim 19, wherein said rotational articulation allows for limited expansion.

21. The push-in implant of claim 17, wherein said rotational articulation is formed by said upper and lower members interdigitating so as to cooperatively engage.

22. The push-in implant of claim 21, wherein said rotational articulation is configured such that engagement occurs when said upper and lower members are substantially perpendicular to one another.

23. The push-in implant of claim 22, wherein said rotational articulation is configured to remain engaged within a range of movement of said upper and lower members resulting from positioning said implant in the second position.

24. The push-in implant of claim 2, wherein one of said upper and lower members has an interior wall, which is unexposed, extending therefrom toward the other of said upper and lower members when said implant is in an initial insertion position, and when said implant is in a final position said implant has a shape such that each of said upper and lower surfaces of said upper and lower members are separated by at least a portion of said interior wall, which now has an exposed side.

25. The push-in implant of claim 24, wherein said upper and lower members have side walls for engaging each other.

26. The push-in implant of claim 25, wherein said side walls of said upper and lower members are at least partially overlapping walls.

27. The push-in implant of claim 24, wherein said upper and lower surfaces of said upper and lower members form an angular orientation relative to one another when said implant is in the final position.

28. The push-in implant of claim 24, wherein said upper and lower surfaces of said upper and lower members are substantially planar and parallel when said implant is in the initial insertion position.

29. The push-in implant of claim 2, wherein said implant has an interior, at least one of said upper and lower surfaces has a screw hole passing therethrough adapted to receive a screw passing from said interior of said implant into one of the adjacent vertebral bodies.

30. The push-in implant of claim 29, wherein each of said upper and lower surfaces has at least one screw hole passing therethrough adapted to receive a screw passing from said interior of said implant into the adjacent vertebral body in contact with each of said upper and lower surfaces respectively.

31. The push-in implant of claim 29, further comprising at least one screw adapted to pass from said interior of said implant through said screw hole and into the adjacent vertebral body to anchor said implant to the adjacent vertebral body.

32. The push-in implant of claim 2, wherein said implant has a side surface when in a final position that is contoured to cooperate with another implant.

33. The push-in implant of claim 2, further comprising a cap for closing one of said proximal end and said distal end of said upper and lower members, said cap having an exterior surface and an interior surface.

34. The push-in implant of claim 33, wherein said interior surface of said cap has spaced slots about its circumference to facilitate a snap fit of said cap into said implant.

35. The push-in implant of claim 2, wherein said implant comprises an artificial material other than bone.

36. The push-in implant of claim 2, wherein said implant is made of an artificial material that is stronger than bone.

37. The push-in implant of claim 2, wherein said implant is made of an artificial material that is harder than bone.

38. The push-in implant of claim 2, wherein said implant comprises bone.

39. The push-in implant of claim 38, wherein said bone includes cortical bone.

40. The push-in implant of claim 2, wherein said implant comprises bone growth promoting material.

41. The push-in implant of claim 40, wherein said bone growth promoting material includes at least one of bone morphogenetic protein, hydroxyapatite, and genes coding for the production of bone.

42. The push-in implant of claim 2, wherein said implant is treated with a bone growth promoting substance.

43. The push-in implant of claim 2, wherein said implant is a source of osteogenesis.

44. The push-in implant of claim 2, wherein said implant is at least in part bioabsorbable.

45. The push-in implant of claim 2, wherein said implant comprises metal.

46. The push-in implant of claim 45, wherein said metal includes titanium.

47. The push-in implant of claim 2, wherein said implant comprises a plastic material.

48. The push-in implant of claim 2, wherein said implant comprises a ceramic material.

49. The push-in implant of claim 2, wherein said implant is formed of a porous material.

50. The push-in implant of claim 2, wherein said implant is formed of a material that intrinsically participates in the growth of bone from adjacent vertebral body to adjacent vertebral body through said implant.

51. The push-in implant of claim 2, wherein said fusion promoting substances include at least one of bone morphogenetic protein, hydroxyapatite, and genes coding for the production of bone.

52. The push-in implant of claim 2, wherein at least a portion of said implant is treated to promote bone ingrowth between said implant and said adjacent vertebral bodies.

53. The push-in implant of claim 2, in combination with a chemical substance to inhibit scar formation.

54. The push-in implant of claim 2, further comprising at least a portion of a bone-engaging projection adapted for linear insertion formed on the exterior of each of said upper and lower surfaces for penetrably engaging the adjacent vertebral bodies and to facilitate securing said implant into the spine.

55. The push-in implant of claim 54, wherein said bone-engaging projection is select from one of a ratchet, a surface roughening, and a knurling.

56. The push-in implant of claim 2, wherein said upper member has side walls extending from said upper surface toward said lower member.

57. The push-in implant of claim 2, wherein said lower member has side walls extending from said lower surface toward said upper member.

58. The push-in implant of claim 2, wherein said upper member has side walls extending from said upper surface toward said lower member and said lower member has side walls extending from said lower surface toward said upper member.

59. The push-in implant of claim 2, wherein said implant is substantially parallelepiped.

60. The push-in implant of claim 1, in combination with a fusion promoting substance.

61. The push-in implant of claim 60, wherein said fusion promoting substance includes at least one of bone, bone morphogenetic protein, hydroxyapatite, and genes coding for the production of bone.

62. The push-in implant of claim 1, in combination with a tool for expanding said implant.

63. The combination of claim 62, wherein said tool is one of a spreader and a distractor.

64. The push-in implant of claim 1, in combination with a tool for inserting said implant at least in part into the disc space.

* * * * *

UNITED STATES PATENT AND TRADEMARK OFFICE
CERTIFICATE OF CORRECTION

PATENT NO. : 6,716,247 B2
DATED : April 6, 2004
INVENTOR(S) : Gary K. Michelson

It is certified that error appears in the above-identified patent and that said Letters Patent is hereby corrected as shown below:

<u>Title page,</u>
Item [*] Notice, "Subject to any disclaimer, ther term of this patent is extended or adjusted under 35 U.S.C. 154(b) by 23 days." should read -- Subject to any disclaimer, ther term of this patent is extended or adjusted under 35 U.S.C. 154(b) by 102 days. --.

Signed and Sealed this

Twenty-fifth Day of October, 2005

JON W. DUDAS
*Director of the United States Patent and Trademark Office*